(12) United States Patent
Schmidt et al.

(10) Patent No.: US 11,850,422 B2
(45) Date of Patent: Dec. 26, 2023

(54) ELECTRODES FOR ELECTRICAL STIMULATION TO TREAT CANCER

(71) Applicant: Boston Scientific Scimed, Inc., Maple Grove, MN (US)

(72) Inventors: Brian L Schmidt, White Bear Lake, MN (US); Devon N. Arnholt, Shoreview, MN (US); Keith R. Maile, New Brighton, MN (US); Sarah Melissa Gruba, Vadnais Heights, MN (US); William J. Linder, Golden Valley, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

(21) Appl. No.: 16/855,433

(22) Filed: Apr. 22, 2020

(65) Prior Publication Data

US 2020/0338345 A1   Oct. 29, 2020

Related U.S. Application Data

(60) Provisional application No. 62/837,390, filed on Apr. 23, 2019.

(51) Int. Cl.
*A61N 1/36* (2006.01)
*A61N 1/05* (2006.01)
(Continued)

(52) U.S. Cl.
CPC .......... *A61N 1/36002* (2017.08); *A61L 31/16* (2013.01); *A61N 1/05* (2013.01); *A61N 1/08* (2013.01)

(58) Field of Classification Search
CPC ........ A61N 1/36002; A61N 1/05; A61N 1/08; A61L 31/16
See application file for complete search history.

(56) References Cited

U.S. PATENT DOCUMENTS

| 4,016,886 A | 4/1977 | Doss et al. |
|---|---|---|
| 5,099,838 A | 3/1992 | Bardy |

(Continued)

FOREIGN PATENT DOCUMENTS

| AU | 2005301103 | 5/2006 |
|---|---|---|
| CN | 101693875 | 4/2010 |

(Continued)

OTHER PUBLICATIONS

"Optune®—Elevate Expectations / Patient Information and Operation Manual," Novocure ™, www.optune.com, 46, pages, Jan. 2019.

(Continued)

*Primary Examiner* — William J Levicky
(74) *Attorney, Agent, or Firm* — Pauly, DeVries Smith & Deffner LLC

(57) ABSTRACT

Embodiments herein relate to medical devices and methods for using the same to treat cancerous tumors within a bodily tissue. A medical device system is included having an electric field generating circuit and control circuitry configured to control delivery of the one or more electric fields from the electric field generating circuit to the site of the cancerous tissue. An implantable lead is included having a lead body including a first electrical conductor disposed within the lead body, and a first electrode coupled to the lead body, the first electrode in electrical communication with the first electrical conductor, wherein the first electrical conductor forms part of an electrical circuit by which the electric fields from the electric field generating circuit are delivered to the site of the cancerous tissue, and the first electrode can include a conductive coil filar disposed around the lead body. Other embodiments are also included herein.

12 Claims, 15 Drawing Sheets

(51) Int. Cl.
  *A61N 1/08* (2006.01)
  *A61L 31/16* (2006.01)

(56) References Cited

U.S. PATENT DOCUMENTS

| | | | |
|---|---|---|---|
| 5,324,328 A * | 6/1994 | Li | A61N 1/0587 607/129 |
| 5,397,342 A | 3/1995 | Heil et al. | |
| 5,458,597 A | 10/1995 | Edwards et al. | |
| 5,582,609 A | 12/1996 | Swanson et al. | |
| 5,834,051 A | 11/1998 | Woloszko et al. | |
| 6,366,808 B1 | 4/2002 | Schroeppel et al. | |
| 6,673,623 B1 | 1/2004 | Huberman | |
| 6,868,289 B2 | 3/2005 | Palti | |
| 6,920,361 B2 | 7/2005 | Williams | |
| 7,524,274 B2 | 4/2009 | Patrick et al. | |
| 7,565,205 B2 | 7/2009 | Palti | |
| 7,656,205 B2 | 2/2010 | Chen et al. | |
| 7,715,921 B2 | 5/2010 | Palti | |
| 7,720,549 B2 | 5/2010 | Schroeppel et al. | |
| 7,805,201 B2 | 9/2010 | Palti | |
| 7,809,441 B2 | 10/2010 | Kane et al. | |
| 7,890,183 B2 | 2/2011 | Palti et al. | |
| 7,917,227 B2 | 3/2011 | Palti | |
| 8,002,821 B2 | 8/2011 | Stinson | |
| 8,019,414 B2 | 9/2011 | Palti | |
| 8,170,648 B2 | 5/2012 | Field et al. | |
| 8,175,698 B2 | 5/2012 | Palti et al. | |
| 8,229,555 B2 | 7/2012 | Palti | |
| RE43,618 E | 8/2012 | Palti | |
| 8,244,345 B2 | 8/2012 | Palti | |
| 8,406,870 B2 | 3/2013 | Palti | |
| 8,447,395 B2 | 5/2013 | Palti et al. | |
| 8,447,396 B2 | 5/2013 | Palti et al. | |
| 8,465,533 B2 | 6/2013 | Palti | |
| 8,483,821 B2 | 7/2013 | Averina et al. | |
| 8,500,713 B2 | 8/2013 | Ferek-Petric | |
| 8,706,261 B2 | 4/2014 | Palti | |
| 8,715,203 B2 | 5/2014 | Palti | |
| 8,718,756 B2 | 5/2014 | Palti | |
| 8,764,675 B2 | 7/2014 | Palti | |
| 8,956,352 B2 | 2/2015 | Mauch et al. | |
| 9,005,100 B2 | 4/2015 | Gnanashanmugam et al. | |
| 9,023,090 B2 | 5/2015 | Palti | |
| 9,023,091 B2 | 5/2015 | Palti | |
| 9,039,674 B2 | 5/2015 | Palti et al. | |
| 9,056,203 B2 | 6/2015 | Palti et al. | |
| 9,248,278 B2 | 2/2016 | Crosby et al. | |
| 9,283,383 B2 | 3/2016 | Osypka | |
| 9,308,039 B2 | 4/2016 | Azure | |
| 9,387,323 B2 | 7/2016 | Fleischhacker et al. | |
| 9,440,068 B2 | 9/2016 | Palti et al. | |
| 9,526,911 B1 | 12/2016 | Azure et al. | |
| 9,630,022 B2 | 4/2017 | Bourke et al. | |
| 9,655,669 B2 | 5/2017 | Palti et al. | |
| 9,750,934 B2 | 9/2017 | Palti et al. | |
| 9,833,617 B2 | 12/2017 | Travers et al. | |
| 9,910,453 B2 | 3/2018 | Wasserman et al. | |
| 10,029,117 B2 | 7/2018 | Bourke | |
| 10,238,862 B2 | 3/2019 | Cook et al. | |
| 10,265,530 B1 | 4/2019 | Perryman et al. | |
| 10,376,177 B2 | 8/2019 | Valvano et al. | |
| 10,471,254 B2 | 11/2019 | Sano et al. | |
| 11,191,956 B2 | 12/2021 | Giladi et al. | |
| 11,331,493 B2 | 5/2022 | Pivonka et al. | |
| 11,338,135 B2 | 5/2022 | Schmidt et al. | |
| 11,420,049 B2 | 8/2022 | Schmidt et al. | |
| 2001/0044643 A1 | 11/2001 | Litovitz | |
| 2002/0049485 A1 | 4/2002 | Smits | |
| 2003/0020416 A1 | 1/2003 | Kobayashi | |
| 2003/0069623 A1 | 4/2003 | Stypulkowski | |
| 2003/0204161 A1 | 10/2003 | Ferek-Petric | |
| 2004/0010290 A1 | 1/2004 | Schroeppel et al. | |
| 2004/0158288 A1 | 8/2004 | Keisari et al. | |
| 2004/0162600 A1 | 8/2004 | Williams | |
| 2004/0176804 A1 | 9/2004 | Palti | |
| 2004/0215296 A1 | 10/2004 | Ganz et al. | |
| 2005/0004507 A1 | 1/2005 | Schroeppel et al. | |
| 2005/0043894 A1 | 2/2005 | Fernandez | |
| 2005/0096584 A1 | 5/2005 | Ferek-Petric | |
| 2005/0209642 A1 | 9/2005 | Palti | |
| 2005/0222623 A1 | 10/2005 | Kroll et al. | |
| 2005/0222646 A1 | 10/2005 | Kroll et al. | |
| 2005/0240173 A1 | 10/2005 | Palti | |
| 2005/0288730 A1 | 12/2005 | Deem et al. | |
| 2006/0024802 A1 | 2/2006 | Muller et al. | |
| 2006/0149341 A1 | 7/2006 | Palti | |
| 2006/0282122 A1 | 12/2006 | Palti | |
| 2007/0033660 A1 | 2/2007 | Palti | |
| 2007/0179550 A1 | 8/2007 | Dennis et al. | |
| 2007/0225766 A1 | 9/2007 | Palti | |
| 2007/0239213 A1 | 10/2007 | Palti | |
| 2007/0239244 A1 | 10/2007 | Morgan et al. | |
| 2007/0270675 A1 | 11/2007 | Kane et al. | |
| 2007/0270916 A1 | 11/2007 | Fischell et al. | |
| 2008/0058669 A1 | 3/2008 | Kroll | |
| 2008/0071350 A1 * | 3/2008 | Stinson | A61F 2/915 623/1.15 |
| 2008/0086073 A1 | 4/2008 | McDaniel | |
| 2008/0195227 A1 | 8/2008 | Boling et al. | |
| 2008/0208271 A1 * | 8/2008 | Sih | A61N 1/3621 607/5 |
| 2008/0275524 A1 | 11/2008 | Furness et al. | |
| 2009/0076500 A1 | 3/2009 | Azure et al. | |
| 2009/0192381 A1 | 7/2009 | Brockway et al. | |
| 2009/0234211 A1 | 9/2009 | Li et al. | |
| 2010/0016936 A1 | 1/2010 | Stevenson et al. | |
| 2010/0198298 A1 | 8/2010 | Schulman et al. | |
| 2010/0261994 A1 | 10/2010 | Davalos et al. | |
| 2010/0298895 A1 | 11/2010 | Ghaffari et al. | |
| 2010/0331938 A1 | 12/2010 | Sommer et al. | |
| 2011/0071608 A1 | 3/2011 | Fleischhacker et al. | |
| 2011/0125215 A1 | 5/2011 | Goetz et al. | |
| 2011/0137229 A1 | 6/2011 | Palti et al. | |
| 2011/0238057 A1 | 9/2011 | Moss et al. | |
| 2012/0035616 A1 | 2/2012 | Olsen et al. | |
| 2012/0130444 A1 | 5/2012 | Wei et al. | |
| 2012/0158072 A1 | 6/2012 | Venook et al. | |
| 2012/0158122 A1 * | 6/2012 | Mattson | A61F 2/856 623/1.15 |
| 2012/0203307 A1 | 8/2012 | Schroeppel et al. | |
| 2012/0232615 A1 | 9/2012 | Barolat et al. | |
| 2012/0283726 A1 | 11/2012 | Palti | |
| 2013/0023946 A1 | 1/2013 | Valvano et al. | |
| 2013/0165916 A1 | 6/2013 | Mathur et al. | |
| 2013/0204068 A1 * | 8/2013 | Gnanashanmugam | A61B 18/04 601/3 |
| 2013/0261706 A1 | 10/2013 | Mirro et al. | |
| 2013/0261711 A1 | 10/2013 | Sivo | |
| 2013/0289649 A1 | 10/2013 | Averina et al. | |
| 2013/0289664 A1 | 10/2013 | Johanek | |
| 2013/0310898 A1 | 11/2013 | Ollivier et al. | |
| 2014/0005753 A1 | 1/2014 | Carbunaru | |
| 2014/0052227 A1 | 2/2014 | Wahlstrand et al. | |
| 2014/0107511 A1 | 4/2014 | Banet et al. | |
| 2014/0350653 A1 | 11/2014 | Shiroff et al. | |
| 2015/0005804 A1 | 1/2015 | Franano et al. | |
| 2015/0066024 A1 | 3/2015 | Azure | |
| 2015/0134022 A1 | 5/2015 | Lee et al. | |
| 2015/0180161 A1 | 6/2015 | Olson et al. | |
| 2015/0182282 A1 | 7/2015 | Zemel et al. | |
| 2015/0320995 A1 | 11/2015 | Nazareth et al. | |
| 2015/0374992 A1 | 12/2015 | Crosby et al. | |
| 2016/0022986 A1 | 1/2016 | Travers et al. | |
| 2016/0029960 A1 | 2/2016 | Toth et al. | |
| 2016/0068598 A1 | 3/2016 | Yan et al. | |
| 2016/0082258 A1 | 3/2016 | Kramer et al. | |
| 2016/0128767 A1 | 5/2016 | Azamian et al. | |
| 2016/0129276 A1 | 5/2016 | Fried et al. | |
| 2016/0250476 A1 | 9/2016 | Kaemmerer et al. | |
| 2016/0250483 A1 | 9/2016 | Klimovitch et al. | |
| 2016/0331459 A1 | 11/2016 | Townley et al. | |
| 2016/0346536 A1 | 12/2016 | Palti et al. | |

(56) References Cited

U.S. PATENT DOCUMENTS

| | | | |
|---|---|---|---|
| 2017/0007310 A1 | 1/2017 | Rajagopalan et al. | |
| 2017/0035496 A1* | 2/2017 | Nagale | A61N 1/36007 |
| 2017/0049514 A1 | 2/2017 | Cosman | |
| 2017/0105793 A1 | 4/2017 | Cao et al. | |
| 2017/0120041 A1 | 5/2017 | Wenger et al. | |
| 2017/0173340 A1 | 6/2017 | Gupte et al. | |
| 2017/0189098 A1 | 7/2017 | Azure et al. | |
| 2017/0215939 A1 | 8/2017 | Palti et al. | |
| 2017/0251976 A1 | 9/2017 | Schouenborg | |
| 2017/0266371 A1 | 9/2017 | Leonhardt et al. | |
| 2017/0281934 A1 | 10/2017 | Giladi et al. | |
| 2017/0281955 A1 | 10/2017 | Maile et al. | |
| 2017/0312501 A1 | 11/2017 | Bornzin et al. | |
| 2017/0333702 A1 | 11/2017 | Barner | |
| 2018/0001075 A1 | 1/2018 | Kirson et al. | |
| 2018/0001078 A1 | 1/2018 | Kirson et al. | |
| 2018/0008708 A1 | 1/2018 | Giladi et al. | |
| 2018/0021563 A1 | 1/2018 | Van De Stolpe et al. | |
| 2018/0050200 A1 | 2/2018 | Wasserman et al. | |
| 2018/0110978 A1 | 4/2018 | Beebe et al. | |
| 2018/0154142 A1 | 6/2018 | Guo et al. | |
| 2018/0221088 A1 | 8/2018 | Govari et al. | |
| 2018/0246079 A1 | 8/2018 | Wang et al. | |
| 2018/0289954 A1 | 10/2018 | Hebb et al. | |
| 2019/0117969 A1 | 4/2019 | Schmidt et al. | |
| 2019/0117970 A1 | 4/2019 | Schmidt et al. | |
| 2019/0117971 A1 | 4/2019 | Schmidt et al. | |
| 2019/0117972 A1* | 4/2019 | Schmidt | A61N 1/36002 |
| 2019/0117973 A1 | 4/2019 | Schmidt et al. | |
| 2019/0255344 A1 | 8/2019 | Carter et al. | |
| 2020/0009377 A1 | 1/2020 | Chang et al. | |
| 2020/0330756 A1 | 10/2020 | Schmidt et al. | |
| 2020/0330757 A1 | 10/2020 | Schmidt et al. | |
| 2020/0330758 A1 | 10/2020 | Schmidt et al. | |
| 2020/0338344 A1 | 10/2020 | Schmidt et al. | |
| 2020/0338346 A1 | 10/2020 | Schmidt et al. | |
| 2021/0260370 A1 | 8/2021 | Srivastava et al. | |
| 2022/0241586 A1 | 8/2022 | Spehr et al. | |
| 2022/0296907 A1 | 9/2022 | Schmidt et al. | |

FOREIGN PATENT DOCUMENTS

| | | | |
|---|---|---|---|
| CN | 202365923 | | 8/2012 |
| CN | 204698678 | | 10/2015 |
| CN | 106823145 | A | 6/2017 |
| CN | 111263618 | | 6/2020 |
| CN | 111263656 | | 6/2020 |
| CN | 111278504 | | 6/2020 |
| CN | 111432872 | | 7/2020 |
| CN | 111465429 | | 7/2020 |
| EP | 2942023 | | 11/2015 |
| EP | 3700451 | | 9/2020 |
| EP | 3700621 | | 9/2020 |
| EP | 3700623 | | 9/2020 |
| EP | 3700626 | | 9/2020 |
| EP | 3700627 | | 9/2020 |
| TW | 201039699 | | 11/2010 |
| WO | 9513113 | | 5/1995 |
| WO | 9526911 | | 10/1995 |
| WO | 0158371 | | 8/2001 |
| WO | 0167098 | | 9/2001 |
| WO | 2005115535 | | 12/2005 |
| WO | 2006047833 | | 5/2006 |
| WO | WO-2008089360 A1 * | 7/2008 | ........... A61N 1/0556 |
| WO | 2009036457 | | 3/2009 |
| WO | 2009036459 | | 3/2009 |
| WO | 2013052590 | | 4/2013 |
| WO | 2015100451 A1 | | 7/2015 |
| WO | WO-2015175570 A1 * | 11/2015 | ........... A61B 18/1206 |
| WO | 2016065263 | | 4/2016 |
| WO | 2016149575 | | 9/2016 |
| WO | 2016168485 | | 10/2016 |
| WO | 2016179712 | | 11/2016 |
| WO | 2016199142 | | 12/2016 |
| WO | 2017123981 A1 | | 7/2017 |
| WO | 2018207103 | | 11/2018 |
| WO | 2019084003 | | 5/2019 |
| WO | 2019084011 | | 5/2019 |
| WO | 2019084013 | | 5/2019 |
| WO | 2019084016 | | 5/2019 |
| WO | 2019084021 | | 5/2019 |
| WO | 2020219336 | | 10/2020 |
| WO | 2020219337 | | 10/2020 |
| WO | 2020219339 | | 10/2020 |
| WO | 2020219517 | | 10/2020 |
| WO | 2020219519 | | 10/2020 |
| WO | 2020219521 | | 10/2020 |

OTHER PUBLICATIONS

Di Sebastiano, Andrea R. et al., "Preclinical Outcomes of Intratumoral Modulation Therapy for Glioblastoma," Scientific Reports (2018) 8:7301 (11 pages).

File History for U.S. Appl. No. 16/166,957 downloaded Dec. 28, 2020 (427 pages).

File History for U.S. Appl. No. 16/167,079 downloaded Dec. 28, 2020 (301 pages).

File History for U.S. Appl. No. 16/167,087 downloaded Dec. 28, 2020 (310 pages).

File History for U.S. Appl. No. 16/167,116 downloaded Dec. 28, 2020 (238 pages).

File History for U.S. Appl. No. 16/167,140 downloaded Dec. 28, 2020 (231 pages).

"First Examination Report," for Australian Patent Application No. 2018354149 dated Jul. 29, 2020 (5 pages).

"First Examination Report," for Australian Patent Application No. 2018354157 dated Jul. 31, 2020 (5 pages).

"First Examination Report," for Australian Patent Application No. 2018354159 dated Aug. 12, 2020 (5 pages).

"First Examination Report," for Australian Patent Application No. 2018354162 dated Sep. 29, 2020 (8 pages).

"First Examination Report," for Australian Patent Application No. 2018354167 dated Sep. 14, 2020 (5 pages).

"International Preliminary Report on Patentability," for PCT Application No. PCT/US2018/057104 dated May 7, 2020 (8 pages).

"International Preliminary Report on Patentability," for PCT Application No. PCT/US2018/057115 dated May 7, 2020 (9 pages).

"International Preliminary Report on Patentability," for PCT Application No. PCT/US2018/057117 dated May 7, 2020 (8 pages).

"International Preliminary Report on Patentability," for PCT Application No. PCT/US2018/057120 dated May 7, 2020 (8 pages).

"International Preliminary Report on Patentability," for PCT Application No. PCT/US2018/057127 dated May 7, 2020 (8 pages).

"International Search Report and Written Opinion," for PCT Application No. PCT/US2018/057104 dated Dec. 20, 2018 (14 pages).

"International Search Report and Written Opinion," for PCT Application No. PCT/US2018/057115 dated Jan. 4, 2019 (13 pages).

"International Search Report and Written Opinion," for PCT Application No. PCT/US2018/057117 dated Dec. 20, 2018 (14 pages).

"International Search Report and Written Opinion," for PCT Application No. PCT/US2018/057120 dated Dec. 19, 2018 (14 pages).

"International Search Report and Written Opinion," for PCT Application No. PCT/US2018/057127 dated Jan. 18, 2019 (12 pages).

"International Search Report and Written Opinion," for PCT Application No. PCT/US2020/028508 dated Aug. 3, 2020 (13 pages).

"International Search Report and Written Opinion," for PCT Application No. PCT/US2020/028509 dated Jun. 30, 2020 (15 pages).

"International Search Report and Written Opinion," for PCT Application No. PCT/US2020/028512 dated Jul. 13, 2020 (14 pages).

"International Search Report and Written Opinion," for PCT Application No. PCT/US2020/029270 dated Oct. 26, 2020 (19 pages).

"International Search Report and Written Opinion," for PCT Application No. PCT/US2020/029274 dated Aug. 28, 2020 (19 pages).

"International Search Report and Written Opinion," for PCT Application No. PCT/US2020/029277 dated Jul. 13, 2020 (15 pages).

"Invitation to Pay Additional Fees," for PCT Application No. PCT/US2020/029270 dated Aug. 28, 2020 (14 pages).

(56) References Cited

OTHER PUBLICATIONS

"Invitation to Pay Additional Fees," for PCT Application No. PCT/US2020/029274 dated Jul. 7, 2020 (13 pages).
Kirson, Eilon D. et al., "Disruption of Cancer Cell Replication by Alternating Electric Fields," Cancer Research 64, 3288-3295, May 1, 2004 (8 pages).
"Novocure Announces Launch of the inovitro™," Laboratory Research System, Press Release, 2 pages, Nov. 21, 2013., 2 pages.
"Response to Communication Pursuant to Rules 161(1) and 162 EPC," for European Patent Application No. 18800411.3 filed Dec. 9, 2020 (11 pages).
"Response to Communication Pursuant to Rules 161(1) and 162 EPC," for European Patent Application No. 18801134.0 filed Dec. 11, 2020 (9 pages).
"Response to Communication Pursuant to Rules 161(1) and 162 EPC," for European Patent Application No. 18801136.5 filed Dec. 10, 2020 (8 pages).
"Response to Communication Pursuant to Rules 161 (1) and 162 EPC," for European Patent Application No. 18801137.3 filed Dec. 10, 2020 (7 pages).
"Response to Communication Pursuant to Rules 161(1) and 162 EPC," for European Patent Application No. 18801138.1 filed Dec. 11, 2020 (16 pages).
"Response to Examination Report," for Australian Patent Application No. 2018354149 filed Dec. 21, 2020 (14 pages).
Wang, Lijun et al., "Tumour Cell Membrane Poration and Ablation by Pulsed Low-Intensity Electric Field with Carbon Nanotubes," Int. J. Mol. Sci. 2015, 16, 6890-6901 (12 pages).
Xu, Hu et al., "In Vitro Validation of Intratumoral Modulation Therapy for Glioblastoma," Anticancer Research 36:71-80 (2016), 10 pages.
"Communication Pursuant to Article 94(3) EPC," for European Patent Application No. 18801138.1 dated Jun. 7, 2021 (7 pages).
"Examination Report," for Australian Patent Application No. 2018354162 dated Apr. 21, 2021 (5 pages).
"Examination Report," for Canadian Patent Application No. 3,079,213 dated Jul. 12, 2021 (4 pages).
"Examination Report," for Canadian Patent Application No. 3,079,282 dated Jul. 14, 2021 (4 pages).
"Examination Report," for Canadian Patent Application No. 3,079,314 dated Jul. 14, 2021 (4 pages).
"Final Office Action," for U.S. Appl. No. 16/166,957 dated May 14, 2021 (33 pages).
"Final Office Action," for U.S. Appl. No. 16/167,079 dated Jun. 23, 2021 (34 pages).
"First Office Action," for Chinese Patent Application No. 201880068896.3 dated Apr. 13, 2021 (17 pages) with English Summary.
"International Search Report and Written Opinion," for PCT Application No. PCT/US2021/019160 dated Jun. 2, 2021 (15 pages).
"Non-Final Office Action," for U.S. Appl. No. 16/167,087 dated Mar. 31, 2021 (28 pages).
"Non-Final Office Action," for U.S. Appl. No. 16/167,140 dated Jul. 12, 2021 (32 pages).
"Non-Final Office Action," for U.S. Appl. No. 16/855,421 dated May 28, 2021 (37 pages).
"Office Action," for Canadian Patent Application No. 3,079,289 dated May 28, 2021 (4 pages).
"Office Action," for Japanese Patent Application No. 2020-542719 dated Jun. 1, 2021 (9 pages) with English Translation.
"Office Action," for Japanese Patent Application No. 2020-542720 dated May 11, 2021 (13 pages) with English Translation.
"Response to Examination Report," for Australian Patent Application No. 2018354162 filed Jul. 13, 2021 (18 pages).
"Response to Examination Report," for Australian Patent Application No. 2018354162 filed Mar. 30, 2021 (15 pages).
"Response to Non-Final Rejection," dated Jan. 6, 2021 for U.S. Appl. No. 16/267,079, submitted via EFS-Web on Apr. 6, 2021, 19 pages.
"Response to Non-Final Rejection," mailed on Mar. 31, 2021 for U.S. Appl. No. 16/167,087, submitted via EFS-Web on Jun. 23, 2021, 12 pages.
"Response to Second Examination Report," for Australian Patent Application No. 2018354149 filed Apr. 13, 2021 (19 pages).
"Communication Pursuant to Article 94(3) EPC," for European Patent Application No. 18801137.3 dated Mar. 5, 2021 (4 pages).
"Examination Report," for Australian Patent Application No. 2018354162 dated Feb. 4, 2021 (5 pages).
"Final Office Action," for U.S. Appl. No. 16/167,116 dated Jan. 21, 2021 (25 pages).
Giladi, Moshe et al., "Mitotic Spindle Disruption by Alternating Electric Fields Leads to Improper Chromosome Segregation and Mitotic Catastrophe in Cancer Cells," Sci Rep 5, 18046 (2016), 16 pages.
"Non-Final Office Action," for U.S. Appl. No. 16/166,957 dated Feb. 17, 2021 (37 pages).
"Non-Final Office Action," for U.S. Appl. No. 16/167,079 dated Jan. 6, 2021 (28 pages).
"Office Action," for Japanese Patent Application No. 2020-542718 dated Feb. 9, 2021 11 pages) with English Translation.
"Office Action," for Japanese Patent Application No. 2020-542721 dated Feb. 9, 2021 (10 pages) with English Summary.
"Office Action," for Japanese Patent Application No. 2020-542722 dated Feb. 9, 2021 (5 pages) with English Summary.
"Response to Examination Report," for Australian Patent Application No. 2018354157 filed Dec. 31, 2020 (17 pages).
"Response to Examination Report," for Australian Patent Application No. 2018354159 filed Jan. 18, 2021 (21 pages).
"Response to Examination Report," for Australian Patent Application No. 2018354162 filed Jan. 28, 2021 (15 pages).
"Response to Examination Report," for Australian Patent Application No. 2018354167 filed Jan. 28, 2021 (17 pages).
"Response to Final Rejection," dated Jan. 21, 2021 for U.S. Appl. No. 16/167,116, submitted via EFS-Web on Mar. 2, 2021, 12 pages.
"Response to Final Rejection," dated Oct. 13, 2020 for U.S. Appl. No. 16/167,087, 11 pages, submitted via EFS-Web on Jan. 13, 2021.
"Response to Final Rejection," dated Oct. 19, 2020 for U.S. Appl. No. 16/167,140, submitted via EFS-Web on Jan. 19, 2021, 16 pages.
"Response to Non-Final Rejection," dated Feb. 17, 2021 for U.S. Appl. No. 16/166,957, submitted via EFS-Web on Mar. 17, 2021, 17 pages.
"Response to Non-Final Rejection," dated Oct. 7, 2020 for U.S. Appl. No. 16/167,116, submitted via EFS-Web on Jan. 6, 2021, 13 pages.
"Second Examination Report," for Australian Patent Application No. 2018354149 dated Jan. 8, 2021 (4 pages).
"Communication Pursuant to Article 94(3) EPC," for European Patent Application No. 18801137.3 dated Sep. 15, 2021 (4 pages).
"Decision of Rejection," for Japanese Patent Application No. 2020-542719 dated Oct. 19, 2021 (3 pages) No English Translation.
"Final Office Action," for U.S. Appl. No. 16/167,087 dated Aug. 2, 2021 (25 pages).
"First Office Action," for Chinese Patent Application No. 201880078117.8 dated Jul. 20, 2021 (14 pages) with English Summary.
"Non-Final Office Action," for U.S. Appl. No. 16/167,116 dated Sep. 3, 2021 (29 pages).
"Non-Final Office Action," for U.S. Appl. No. 16/850,720 dated Aug. 24, 2021 (32 pages).
"Office Action," for Japanese Patent Application No. 2020-542718 dated Oct. 19, 2021 (3 pages) No English Translation.
"Office Action," for Japanese Patent Application No. 2020-542722 dated Oct. 26, 2021 (5 pages) No English Translation.
"Response to Communication Pursuant to Article 94(3) EPC," for European Patent Application No. 18801138.1 filed Oct. 15, 2021 (10 pages).
"Response to Final Rejection," dated Aug. 2, 2021 for U.S. Appl. No. 16/167,087, submitted via EFS-Web on Nov. 1, 2021, 12 pages.
"Response to Final Rejection," dated Jun. 23, 2021 and the Advisory Action dated Oct. 15, 2021 for U.S. Appl. No. 16/167,079, submitted via EFS-Web on Oct. 21, 2021, 19 pages.

(56) References Cited

OTHER PUBLICATIONS

"Response to Final Rejection," dated Jun. 23, 2021 for U.S. Appl. No. 16/167,079, submitted via EFS-Web on Sep. 9, 2021, 16 pages.
"Response to Final Rejection," dated May 14, 2021 and Advisory Action dated Aug. 26, 2021 for U.S. Appl. No. 16/166,957, submitted via EFS-Web on Sep. 10, 2021.
"Response to Final Rejection," dated May 14, 2021 for U.S. Appl. No. 16/166,957, submitted via EFS-Web on Aug. 5, 2021, 18 pages.
"Response to Non-Final Rejection," dated Aug. 24, 2021 for U.S. Appl. No. 16/850,720, submitted via EFS-Web on Nov. 1, 2021, 11 pages.
"Response to Non-Final Rejection," dated Jul. 12, 2021 for U.S. Appl. No. 16/167,140, submitted via EFS-Web on Oct. 12, 2021, 16 pages.
"Response to Non-Final Rejection," dated May 28, 2021 for U.S. Appl. No. 16/855,421, submitted via EFS-Web on Aug. 20, 2021, 11 pages.
"Response to Office Action," for Canadian Patent Application No. 3,079,289 filed with CIPO Sep. 23, 2021 (17 pages).
"Decision of Rejection," for Japanese Patent Application No. 2020-54219 dated Oct. 19, 2021 (6 pages) with English Translation.
"Final Office Action," for U.S. Appl. No. 16/167,140 dated Dec. 27, 2021 (30 pages).
"Final Office Action," for U.S. Appl. No. 16/850,720 dated Nov. 15, 2021 (15 pages).
"Final Office Action," for U.S. Appl. No. 16/855,421 dated Nov. 5, 2021 (25 pages).
"International Preliminary Report on Patentability," for PCT Application No. PCT/US2020/028508 dated Nov. 4, 2021 (8 pages).
"International Preliminary Report on Patentability," for PCT Application No. PCT/US2020/028509 dated Nov. 4, 2021 (9 pages).
"International Preliminary Report on Patentability," for PCT Application No. PCT/US2020/028512 dated Nov. 4, 2021 (8 pages).
"International Preliminary Report on Patentability," for PCT Application No. PCT/US2020/029270 dated Nov. 4, 2021 (11 pages).
"International Preliminary Report on Patentability," for PCT Application No. PCT/US2020/029274 dated Nov. 4, 2021 (13 pages).
"International Preliminary Report on Patentability," for PCT Application No. PCT/US2020/029277 dated Nov. 4, 2021 (10 pages).
"Non-Final Office Action," for U.S. Appl. No. 16/166,957 dated Dec. 22, 2021 (39 pages).
"Non-Final Office Action," for U.S. Appl. No. 16/167,087 dated Dec. 22, 2021 (24 pages).
"Office Action," for Canadian Patent Application No. 3,079,316 dated Oct. 27, 2021 (4 pages).
"Response to Examination Report," for Canadian Patent Application No. 3,079,213 filed Nov. 10, 2021 (13 pages).
"Response to Examination Report," for Canadian Patent Application No. 3,079,282 filed Nov. 10, 2021 (13 pages).
"Response to Non-Final Rejection," dated Sep. 3, 2021 for U.S. Appl. No. 16/167,116, submitted via EFS-Web on Nov. 2, 2021, 14 pages.
"Response to Office Action," for Canadian Patent Application No. 3,079,314 filed Nov. 12, 2021 (14 pages).
"Response to Office Action," for Canadian Patent Application No. 3,079,316 filed Dec. 31, 2021 (15 pages).
"Second Office Action," for Chinese Patent Application No. 201880068896.3 Oct. 20, 2021 (6 pages), No English translation.
"Non-Final Office Action," for U.S. Appl. No. 16/167,079 dated Feb. 17, 2022 (37 pages).
"Non-Final Office Action," for U.S. Appl. No. 16/850,712 dated Jan. 21, 2022 (40 pages).
"Non-Final Office Action," for U.S. Appl. No. 17/182,436 dated Feb. 1, 2022 (41 pages).
"Notice of Allowance," for U.S. Appl. No. 16/167,116 dated Jan. 26, 2022 (19 pages).
"Notice of Allowance," for U.S. Appl. No. 16/850,720 dated Apr. 14, 2022 (17 pages).
"Office Action," for Canadian Patent Application No. 3,079,289 dated Mar. 24, 2022 (8 pages).
"Office Action," for Japanese Patent Application No. 2020-542721 dated Jan. 4, 2022 (3 pages) with English summary.
"Response to Communication Pursuant to Art. 94(3) EPC," for European Patent Application No. 18801137.3 filed Jan. 13, 2022 (8 pages).
"Response to Final Rejection," daated Dec. 27, 2021 and Advisory Action dated Mar. 9, 2022 for U.S. Appl. No. 16/167,140, submitted via EFS-Web on Mar. 25, 2022, 11 pages.
"Response to Final Rejection," dated Dec. 27, 2021 for U.S. Appl. No. 16/167,140, submitted via EFS-Web on Feb. 9, 2022, 9 pages.
"Response to Final Rejection," dated Nov. 15, 2021 for U.S. Appl. No. 16/850,720, submitted via EFS-Web on Feb. 11, 2022, 12 pages.
"Response to Final Rejection," dated Nov. 5, 2021 and Advisory Action dated Feb. 9, 2022 for U.S. Appl. No. 16/855,421, submitted via EFS-Web on Mar. 4, 2022, 11 pages.
"Response to Final Rejection," dated Nov. 5, 2021 for U.S. Appl. No. 16/855,421, submitted via EFS-Web on Jan. 5, 2022, 11 pages.
"Response to Non-Final Rejection," dated Dec. 22, 2021 for U.S. Appl. No. 16/166,957, submitted via EFS-Web on Mar. 22, 2022, 13 pages.
"Response to Non-Final Rejection," dated Dec. 22, 2021 for U.S. Appl. No. 16/167,087, submitted via EFS-Web on Mar. 22, 2022, 9 pages.
"Response to Non-Final Rejection," dated Feb. 1, 2022 for U.S. Appl. No. 17/182,436, submitted via EFS-Web on Mar. 21, 2022, 8 pages.
"Response to Non-Final Rejection," dated Jan. 21, 2022 for U.S. Appl. No. 16/850,712, submitted via EFS-Web on Mar. 21, 2022, 10 pages.
"Communication Pursuant to Article 94(3) EPC," for European Patent Application No. 18801138.1 dated Aug. 29, 2022 (5 pages).
"International Preliminary Report on Patentability," for PCT Application No. PCT/US2021/019160 dated Sep. 9, 2022 (10 pages).
"Non-Final Office Action," for U.S. Appl. No. 16/166,957 dated Sep. 29, 2022 (41 pages).
"Non-Final Office Action," for U.S. Appl. No. 16/167,087 dated Sep. 15, 2022 (24 pages).
"Notice of Opposition," for European Patent No. 3700627 filed Aug. 24, 2022 (20 pages).
"Response to Final Rejection," dated Jul. 22, 2022 with Request for Continued Examination, for U.S. Appl. No. 17/182,436, submitted via EFS-Web on Sep. 29, 2022, 9 pages.
"Response to Final Rejection," dated Jul. 27, 2022 for U.S. Appl. No. 17/182,436, submitted via EFS-Web on Sep. 27, 2022, 9 pages.
"Response to Final Rejection," dated Jul. 5, 2022 and Advisory Action dated Sep. 15, 2022 for U.S. Appl. No. 16/850,712, submitted via EFS-Web on Sep. 23, 2022, 10 pages.
"Response to Final Rejection," dated Jul. 5, 2022 for U.S. Appl. No. 16/850,712, submitted via EFS-Web on Sep. 6, 2022, 10 pages.
"Response to Final Rejection," dated May 27, 2022 for U.S. Appl. No. 16/167,079, submitted via EFS-Web on Aug. 26, 2022, 12 pages.
"Response to Non-Final Rejection," dated Jun. 7, 2022 for U.S. Appl. No. 16/855,421, submitted via EFS-Web on Sep. 7, 2022, 9 pages.
"Response to Non-Final Rejection," dated May 27, 2022 for U.S. Appl. No. 16/167,140, submitted via EFS-Web on Aug. 25, 2022, 14 pages.
"Non-Final Office Action," for U.S. Appl. No. 16/850,712 dated Oct. 6, 2022 (11 pages).
"Final Office Action," for U.S. Appl. No. 16/166,957 dated May 18, 2022 (35 pages).
"Final Office Action," for U.S. Appl. No. 16/167,079 dated May 27, 2022 (29 pages).
"Final Office Action," for U.S. Appl. No. 16/167,087 dated May 18, 2022 (26 pages).
"Non-Final Office Action," for U.S. Appl. No. 16/167,140 dated May 27, 2022 (25 pages).
"Office Action," for Canadian Patent Application No. 3,079,213 dated Apr. 20, 2022 (6 pages).
"Office Action," for Canadian Patent Application No. 3,079,314 dated Apr. 29, 2022 (3 pages).

(56) References Cited

OTHER PUBLICATIONS

"Response to Communication Pursuant to Rules 161(1) and 162 EPC," for European Patent Application No. 20724332.0 filed May 11, 2022 (24 pages).
"Response to Communication Pursuant to Rules 161(1) and 162 EPC," for European Patent Application No. 20724702.4 filed May 11, 2022 (24 pages).
"Response to Non-Final Rejection," dated Feb. 17, 2022 for U.S. Appl. No. 16/167,079, submitted via EFS-Web on May 3, 2022, 11 pages.
"Response to Communication Pursuant to Rules 161(1) and 162 EPC," for European Patent Application No. 207274176 filed June 1, 2022 (8 pages).
"Final Office Action," for U.S. Appl. No. 16/850,712 dated Jul. 5, 2022 (16 pages).
"Final Office Action," for U.S. Appl. No. 17/182,436 dated Jul. 27, 2022 (19 pages).
"International Search Report and Written Opinion," for PCT Application No. PCT/US2022/021161 dated Jun. 22, 2022 (15 pages).
"Non-Final Office Action," for U.S. Appl. No. 16/855,421 dated Jun. 7, 2022 (21 pages).
"Office Action Response," for Canadian Patent Application No. 3,079,289 filed Jul. 18, 2022 (17 pages).
"Office Action Response," for Canadian Patent Application No. 3,079,314 filed Aug. 11, 2022 (7 pages).
"Office Action," for Canadian Patent Application No. 3,079,316 dated Jun. 3, 2022 (3 pages).
"Response to Communication Pursuant to Rules 161(1) and 162 EPC," for European Patent Application No. 20724703.2 filed Jun. 8, 2022 (12 pages).
"Response to Communication Pursuant to Rules 161(1) and 162 EPC," for European Patent Application No. 20724333.8 filed Jun. 8, 2022 (8 pages).
"Response to Final Rejection," dated May 18, 2022 for U.S. Appl. No. 16/166,957, submitted via EFS-Web on Aug. 18, 2022, 14 pages.
"Response to Final Rejection," dated May 18, 2022 for U.S. Appl. No. 16/167,087, submitted via EFS-Web on Aug. 18, 2022, 9 pages.
"Response to Office Action," for Canadian Patent Application No. 3,079,213 filed Aug. 10, 2022 (10 pages).
"Third Office Action," for Japanese Patent Application No. 2020-542721 dated Aug. 23, 2022 (5 pages) No English Translation.
Notice of Opposition for European Patent Application No. 18801134.0 on behalf of Novocure Gmbh, dated Jun. 28, 2022 (36 pages).
"First Office Action," for Chinese Patent Application No. 201880068897.8 dated Sep. 21, 2022 (11 pages) with English Summary.
"Communication Pursuant to Article 94(3) EPC," for European Patent Application No. 18800411.3 dated Dec. 22, 2022 (5 pages).
"Non-Final Office Action," for U.S. Appl. No. 16/167,140 Nov. 15, 2022 (29 pages).
"Non-Final Office Action," for U.S. Appl. No. 16/850,728 dated Jan. 24, 2023 (68 pages).
"Non-Final Office Action," for U.S. Appl. No. 16/855,448 dated Nov. 7, 2022 (58 pages).
"Non-Final Office Action," for U.S. Appl. No. 17/182,436 dated Nov. 23, 2022 (19 pages).
"Notice of Allowance," For U.S. Appl. No. 16/850,712 dated Feb. 7, 2023 (14 pages).
"Notice of Allowance," for U.S. Appl. No. 16/855,421 dated Nov. 16, 2022 (17 pages).
"Office Action," for Canadian Patent Application No. 3,079,213 dated Dec. 5, 2022 (4 pages).
"Office Action," for Canadian Patent Application No. 3,079,289 dated Nov. 28, 2022 (7 pages).
"Office Action," for Japanese Patent Application No. 2021-562795 dated Nov. 15, 2022 (5 pages) with English Translation.
"Office Action," for Japanese Patent Application No. 2021-562797 dated Nov. 22, 2022 (9 pages), with English Translation.
"Office Action," for Japanese Patent Application No. 2021-562798 dated Nov. 15, 2022 (14 pages), with English translation.
"Office Action," for Japanese Patent Application No. 2021-562966 dated Nov. 29, 2022 (11 pages) with English Translation.
"Office Action," for Japanese Patent Application No. 2021-562972 dated Nov. 8, 2022 (26 pages) with English Translation.
"Response to Communication Pursuant to Rules 161(1) and 162 EPC," for European Patent Application No. 21712639.0 filed Jan. 20, 2023 (26 pages).
"Response to Non-Final Rejection," dated Nov. 15, 2022, based on U.S. Appl. No. 16/167,140, submitted via EFS-Web on Feb. 15, 2023, 12 pages.
"Response to Non-Final Rejection," dated Nov. 7, 2022 for U.S. Appl. No. 16/855,448, submitted via EFS-Web on Feb. 7, 2023, 9 pages.
"Response to Non-Final Rejection," dated Oct. 6, 2022 for U.S. Appl. No. 16/850,712, submitted via EFS-Web on Jan. 4, 2023, 10 pages.
"Response to Non-Final Rejection," dated Sep. 15, 2022 for U.S. Appl. No. 16/167,087, submitted via EFS-Web on Dec. 13, 2022, 8 pages.
"Response to Non-Final Rejection," dated Sep. 29, 2022 for U.S. Appl. No. 16/166,957, submitted via EFS-Web on Dec. 13, 2022, 16 pages.

\* cited by examiner

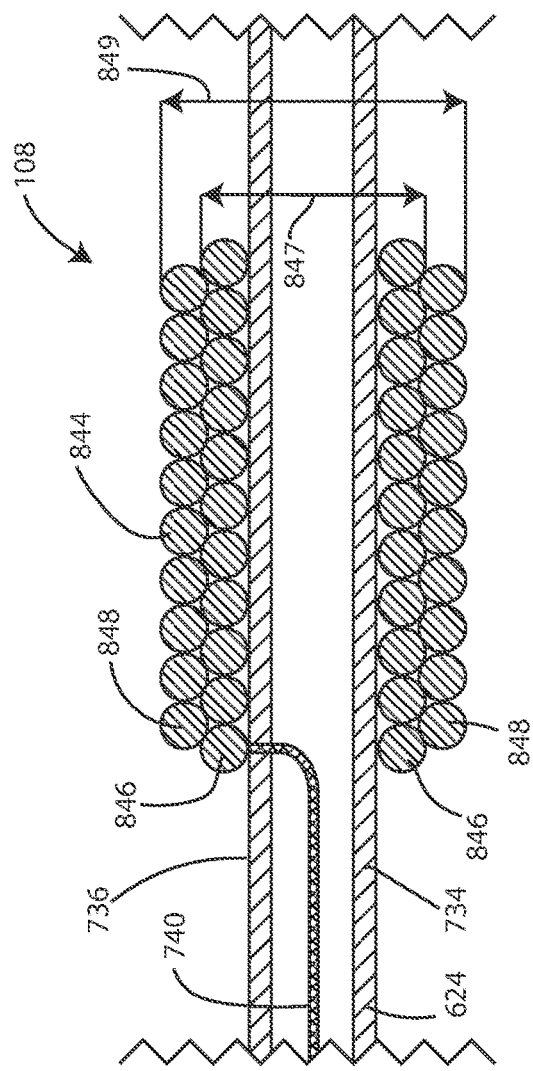
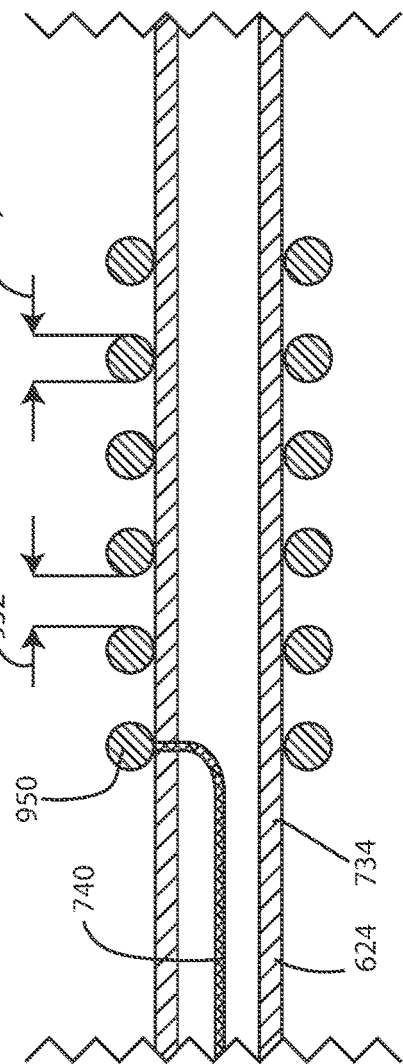
FIG. 8
FIG. 9

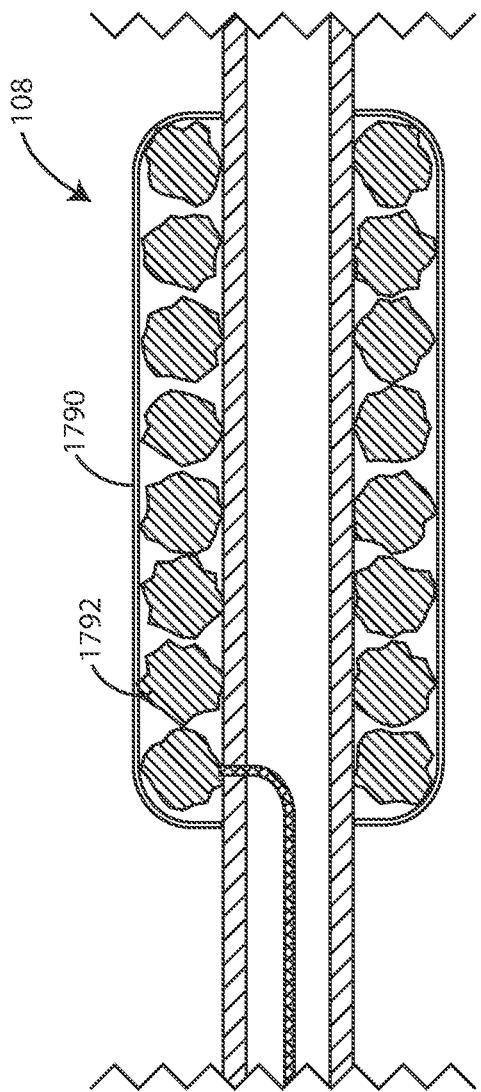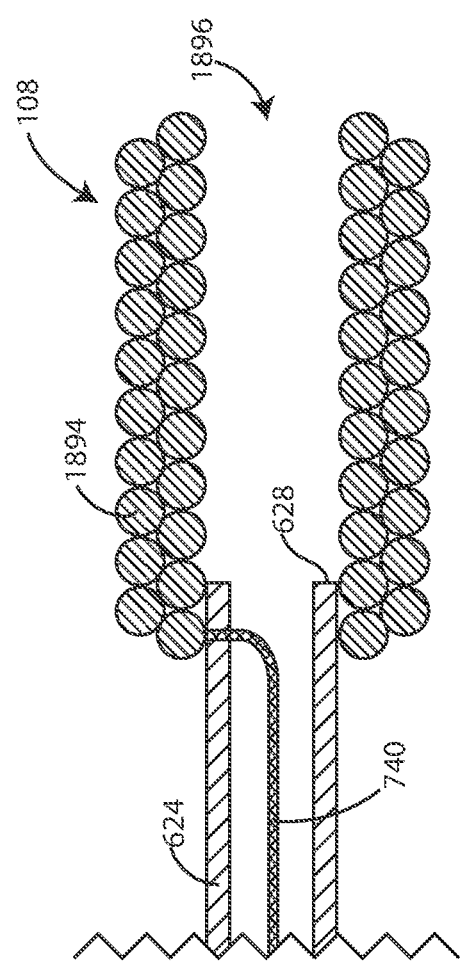

ELECTRODES FOR ELECTRICAL STIMULATION TO TREAT CANCER

This application claims the benefit of U.S. Provisional Application No. 62/837,390, filed Apr. 23, 2019, the content of which is herein incorporated by reference in its entirety.

FIELD

Embodiments herein relate to medical devices and methods for using the same to treat cancerous tumors within a bodily tissue. More specifically, embodiments herein relate to using medical devices with particular electrode designs configured to generate therapeutic electric fields at the site of a cancerous tumor.

BACKGROUND

According to the American Cancer Society, cancer accounts for nearly 25% of the deaths that occur in the United States each year. The current standard of care for cancerous tumors can include first-line therapies such as surgery, radiation therapy, and chemotherapy. Additional second-line therapies can include radioactive seeding, cryotherapy, hormone or biologics therapy, ablation, and the like. Combinations of first-line therapies and second-line therapies can also be a benefit to patients if one particular therapy on its own is not effective.

Cancerous tumors can form if one normal cell in any part of the body mutates and then begins to grow and multiply too much and too quickly. Cancerous tumors can be a result of a genetic mutation to the cellular DNA or RNA that arises during cell division, an external stimulus such as ionizing or non-ionizing radiation, exposure to a carcinogen, or a result of a hereditary gene mutation. Regardless of the etiology, many cancerous tumors are the result of unchecked rapid cellular division.

SUMMARY

In a first aspect, a medical device system for treating a cancerous tissue, is included having an electric field generating circuit configured to generate one or more electric fields at or near a site of the cancerous tissue, a control circuitry in communication with the electric field generating circuit, the control circuitry configured to control delivery of the one or more electric fields from the electric field generating circuit to the site of the cancerous tissue. The control circuitry causes the electric field generating circuit to generate one or more electric fields at frequencies selected from a range of between 10 kHz to 1 MHz. An implantable lead is included having a lead body can include a proximal end and a distal end, the lead body can include a first electrical conductor disposed within the lead body, and a first electrode coupled to the lead body, the first electrode in electrical communication with the first electrical conductor, wherein the first electrical conductor forms part of an electrical circuit by which the electric fields from the electric field generating circuit are delivered to the site of the cancerous tissue, and the first electrode can include a conductive coil filar disposed around the lead body.

In a second aspect, in addition to one or more of the preceding or following aspects, or in the alternative to some aspects, the conductive coil filar can include a first plurality of filars having a first outer diameter and a second plurality of filars having a second outer diameter, wherein the second outer diameter is greater than the first outer diameter and the first plurality of filars overlap the second plurality of filars along a lengthwise axis of the lead body.

In a third aspect, in addition to one or more of the preceding or following aspects, or in the alternative to some aspects, the conductive coil filar can include a pitch between successive filars that is greater than or equal to a diameter of the conductive coil filars.

In a fourth aspect, in addition to one or more of the preceding or following aspects, or in the alternative to some aspects, the conductive coil filar can include a pitch between successive filars is at least twice a diameter of the conductive coil filars.

In a fifth aspect, in addition to one or more of the preceding or following aspects, or in the alternative to some aspects, the conductive coil filar can include a pitch between successive filars is at least four times a diameter of the conductive coil filars.

In a sixth aspect, in addition to one or more of the preceding or following aspects, or in the alternative to some aspects, wherein the conductive coil filar include an irregular surface with increased surface area compared with otherwise identical conductive coil filars having a substantially smooth surface.

In a seventh aspect, in addition to one or more of the preceding or following aspects, or in the alternative to some aspects, wherein the conductive coil filar includes an etched surface.

In an eighth aspect, in addition to one or more of the preceding or following aspects, or in the alternative to some aspects, wherein the conductive coil filar includes a laser-cut surface.

In a ninth aspect, in addition to one or more of the preceding or following aspects, or in the alternative to some aspects, the conductive coil filar can include a first plurality of filars having a first fiber diameter and a second plurality of filars having a second fiber diameter, wherein the second fiber diameter is greater than the first fiber diameter. In a tenth aspect, in addition to one or more of the preceding or following aspects, or in the alternative to some aspects, the conductive coil filar can be configured to expand in outer diameter after removal of a delivery device from over the conductive coil filars.

In an eleventh aspect, in addition to one or more of the preceding or following aspects, or in the alternative to some aspects, the system can include a conductive fluid or gel disposed over the conductive coil filar.

In a twelfth aspect, in addition to one or more of the preceding or following aspects, or in the alternative to some aspects, the system can include an active agent disposed with the conductive fluid or gel.

In a thirteenth aspect, in addition to one or more of the preceding or following aspects, or in the alternative to some aspects, the active agent can include a chemotherapeutic agent or an anti-bacterial agent.

In a fourteenth aspect, a medical device system for treating a cancerous tissue is included having an electric field generating circuit configured to generate one or more electric fields at or near a site of the cancerous tissue and control circuitry in communication with the electric field generating circuit. The control circuitry can be configured to control delivery of the one or more electric fields from the electric field generating circuit to the site of the cancerous tissue, wherein the control circuitry causes the electric field generating circuit to generate one or more electric fields at frequencies selected from a range of between 10 kHz to 1 MHz. An implantable lead can be included having a lead body can include a proximal end and a distal end, the lead body can include a first electrical conductor disposed within lead body and a first electrode coupled to the lead body, the first electrode in electrical communication with the first electrical conductor, wherein the first electrical conductor forms part of an electrical circuit by which the electric fields from the electric field generating circuit are delivered to the site of the cancerous tissue. The first electrode can include a plurality of conductive pillars disposed around the lead body.

In a fifteenth aspect, in addition to one or more of the preceding or following aspects, or in the alternative to some aspects, the plurality of conductive pillars can include tantalum pillars.

In a sixteenth aspect, a medical device system for treating a cancerous tissue, is included having an electric field generating circuit configured to generate one or more electric fields at or near a site of the cancerous tissue and control circuitry in communication with the electric field generating circuit, the control circuitry configured to control delivery of the one or more electric fields from the electric field generating circuit to the site of the cancerous tissue. The control circuitry can cause the electric field generating circuit to generate one or more electric fields at frequencies selected from a range of between 10 kHz to 1 MHz. An implantable lead is included having a lead body can include a proximal end and a distal end, the lead body can include a first electrical conductor disposed within the lead body and a first electrode coupled to the lead body, the first electrode in electrical communication with the first electrical conductor, wherein the first electrical conductor forms part of an electrical circuit by which the electric fields from the electric field generating circuit are delivered to the site of the cancerous tissue and a stent coupled to the lead body at a distal portion thereof.

In a seventeenth aspect, in addition to one or more of the preceding or following aspects, or in the alternative to some aspects, the stent includes a stent frame formed of an electrically conductive material, wherein the stent frame serves as the first electrode.

In an eighteenth aspect, in addition to one or more of the preceding or following aspects, or in the alternative to some aspects, the first electrode is disposed on an outside surface of the stent.

In a nineteenth aspect, in addition to one or more of the preceding or following aspects, or in the alternative to some aspects, the stent includes a stent frame formed of an electrically conductive material and the stent frame is clad with a material resistant to degradation as a result of exposure to electrical currents used to generate the electric fields.

In a twentieth aspect, in addition to one or more of the preceding or following aspects, or in the alternative to some aspects, the stent includes a stent frame formed of an electrically conductive material, wherein the stent frame is coated with a conductive fluid or gel.

This summary is an overview of some of the teachings of the present application and is not intended to be an exclusive or exhaustive treatment of the present subject matter. Further details are found in the detailed description and appended claims. Other aspects will be apparent to persons skilled in the art upon reading and understanding the following detailed description and viewing the drawings that form a part thereof, each of which is not to be taken in a limiting sense. The scope herein is defined by the appended claims and their legal equivalents.

BRIEF DESCRIPTION OF THE FIGURES

Aspects may be more completely understood in connection with the following figures (FIGS.), in which:

FIG. 8 is a cross-sectional schematic view of an electrode in accordance with various embodiments herein.

FIG. 9 is a cross-sectional schematic view of an electrode in accordance with various embodiments herein.

FIG. 17 is a cross-sectional schematic view of an electrode in accordance with various embodiments herein.

FIG. 18 is a cross-sectional schematic view of an electrode in accordance with various embodiments herein.

Figure 1:
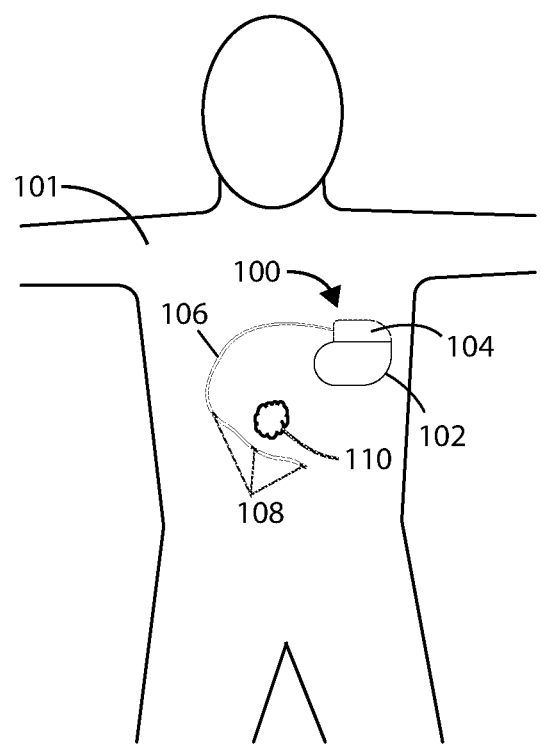
FIG. 1 is a schematic view of a medical system in accordance with various embodiments herein.

While embodiments are susceptible to various modifications and alternative forms, specifics thereof have been shown by way of example and drawings, and will be described in detail. It should be understood, however, that the scope herein is not limited to the particular aspects described. On the contrary, the intention is to cover modifications, equivalents, and alternatives falling within the spirit and scope herein.

DETAILED DESCRIPTION

As referenced above, many cancerous tumors can result from unchecked rapid cellular division. Some traditional first-line therapies to treat cancerous tumors can include surgery, radiation therapy, and chemotherapy. However, many first-line therapies have undesirable concomitant side effects, such as fatigue, hair loss, immunosuppression, and long surgical recovery times, to name a few. In addition, not all patients respond to traditional first-line therapies.

While not intending to be bound by theory, it is believed that electric fields can disrupt mitosis within a cancerous tumor, such as by interfering with the dipole alignment of key proteins involved in cellular division; tubulin and septin in particular. The polymerization of tubulin proteins that form microtubule spindle fibers can be disrupted, thus preventing the formation of spindle fibers required for chromosome separation. This can halt cellular division at the metaphase stage of mitosis. In some instances an electric field can halt polymerization of already growing spindle fibers, leading to incomplete spindles and unequal chromosome separation during anaphase, should the cell survive that long. In each case, halting microtubule spindle formation and unequal chromosome separation during anaphase caused by incomplete polymerization of microtubules, can result in apoptosis (i.e., programmed cell death). It is also believed that alternating electric fields can lead to increased electric field density near the cleavage furrow of the dividing cells during telophase. An increased electric field density in the region of the cleavage furrow can result in dielectrophoresis of charged macromolecules, such as proteins and nucleic acids, toward the high electric field density at the furrow. The unequal concentration of key macromolecules required for cellular division at the site of the cleavage furrow can disrupt the final separation of the sister cells during telophase and eventually lead to apoptosis.

Various embodiments disclosed herein include a medical device system that can generate an electric field for treatment of cancer that can include, or can control, at least one implanted electrode. Implanted electrodes can be advantageous as they can be positioned close to a treatment area (such as a cancerous tumor) and deliver and/or sense an electric field without substantial intervening tissue that diminished field strength.

Larger electrodes can offer superior electrical performance in some scenarios. However, the size of electrodes can be limited when placed in the venous system. In some embodiments herein, an electrode that can double as a stent can provide a large surface area without blocking the venous system.

Various embodiments provided herein can include electrodes that have a high surface area, such as to reduce impedance, lower required voltage, and increase battery longevity. Further, some embodiments herein can include electrodes that can go into a patient's body in a small configuration, but unravel or expand to increase the effect of the electric field once the electrode is in a desired location within the patient.

Electrodes for generating an electric field for cancer treatment are unique. Electrodes for cancer treatment can be utilized more frequently than electrodes that are used for shocking a heart to treat a dangerous arrhythmia. Further, electrodes for cancer treatment can be exposed to more power than electrodes that are used to provide pacing pulses to the heart. Electrodes herein for cancer treatment can be highly stable compared to more common electrodes such as pacing electrodes and/or cardiac shocking electrodes so that the electrodes can deliver an electric field at an increased power and/or frequency, yet prevent the metal in the electrodes from wearing, eroding, or otherwise becoming damaged.

In reference now to FIG. 1, a schematic view is shown of a medical device 100 in accordance with various embodiments herein. The medical device 100 can be implanted entirely within the body of a patient 101 at or near the site of a cancerous tumor 110 located within a bodily tissue. Various implant sites can be used including areas such as in the limbs, the upper torso, the abdominal area, the head, and the like.

Figure 2:
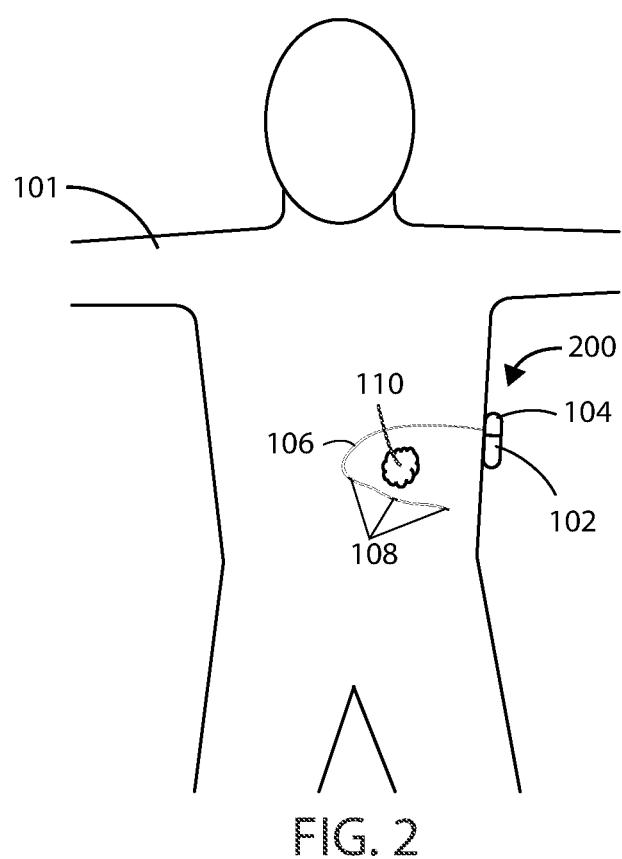
FIG. 2 is a schematic view of a medical system in accordance with various embodiments herein.

In reference now to FIG. 2, another schematic view is shown of a medical device 200 in accordance with various embodiments herein. The medical device 200 can be external, but can be connected to an element, such as leads, that are at least partially implanted within the body of a patient 101. In some embodiments, the medical device 200 can be partially implanted and partially external to the body of a patient. In some embodiments, the medical device 200 can include a transcutaneous connection between components disposed internal to the body and external to the body. In various embodiments, the medical device system described herein can include an implanted medical device 100 and an external medical device 200. In other embodiments, the medical device system described herein can include a partially implanted medical device.

An implanted portion of a medical device system, such as an implanted medical device 100 or portion thereof, can wirelessly communicate patient identification data, diagnostic information, electric field data, physiological parameters, software updates, and the like with a fully or partially external portion of a medical device 200 over a wireless connection. Implanted medical device 100 can also wirelessly communicate with an external device configured to wirelessly charge the medical device utilizing inductance, radio frequency, and acoustic energy transfer techniques, and the like.

In some embodiments, a portion of a medical device or system can be entirely implanted and a portion of the medical device can be entirely external. For example, in some embodiments, one or more electrodes or leads can be entirely implanted within the body, whereas the portion of the medical device that generates an electric field, such as an electric field generator, can be entirely external to the body. It will be appreciated that in some embodiments described herein, the electric field generators described can include many of the same components as and can be configured to perform many of the same functions as a pulse generator. In embodiments where a portion of a medical device is entirely implanted and a portion of the medical device is entirely external, the portion of the medical device that is entirely external can communicate wirelessly with the portion of the medical device that is entirely internal. However, in other embodiments a wired connection can be used for the implanted portion to communication with the external portion.

The implanted medical device 100 and/or the medical device 200 can include a housing 102 and a header 104 coupled to the housing 102. Various materials can be used to form the housing 102. In some embodiments, the housing 102 can be formed of a material such as a metal, ceramic, polymer, composite, or the like. In some embodiments, the housing 102, or one or more portions thereof, can be formed of titanium. The header 104 can be formed of various materials, but in some embodiments the header 104 can be formed of a translucent polymer such as an epoxy material. In some embodiments the header 104 can be hollow. In other embodiments the header 104 can be filled with components and/or structural materials such as epoxy or another material such that it is non-hollow.

In some embodiments where a portion of the medical device 100 or 200 is partially external, the header 104 and housing 102 can be surrounded by a protective casing made of durable polymeric material. In other embodiments, where a portion of a device is partially external, the header 104 and housing 102 can be surrounded by a protective casing made of one or more of a polymeric material, metallic material, and/or glass material.

The header 104 can be coupled to one or more leads 106. The header 104 can serve to provide fixation of the proximal end of one or more leads 106 and electrically couple the one or more leads 106 to one or more components within the housing 102. The one or more leads 106 can include one or more electrodes 108 disposed along the length of the electrical leads 106. In some embodiments, electrodes 108 can include electric field generating electrodes and in other embodiments electrodes 108 can include electric field sensing electrodes. In some embodiments, leads 106 can include both electric field generating and electric field sensing electrodes. In other embodiments, leads 106 can include any number of electrodes that are both electric field sensing and electric field generating. The leads 106 can include one or more conductors therein, such as metal wires, to provide electrical communication between the electrodes and a proximal end (or plug) of the lead. The wires can exist as single strands or fibers or can be multifibrillar such as a cable. The leads 106 can include a shaft, typically formed of a polymeric material or another non-conductive material, within which the conductors therein can pass. The proximal end of the leads 106 can be inserted into the header 104, thereby providing electrical communication between the electrodes 108 and the components inside the housing 102. It will be appreciated that while many embodiments of medical devices herein are designed to function with leads, leadless medical devices that generate electrical fields are also contemplated herein.

In various embodiments, the electrodes 108 can be positioned around or adjacent to a tumor 110, such as a cancerous tumor. The tumor 110 can be positioned within an electric field generated by the electrodes 108.

The electric fields generated by the implanted medical device 100 and/or the medical device 200 can vary. In some embodiments, the implanted medical device 100 and/or the medical device 200 can generate one or more electric fields at frequencies selected from a range of between 10 kHz to 1 MHz.

Figure 3:
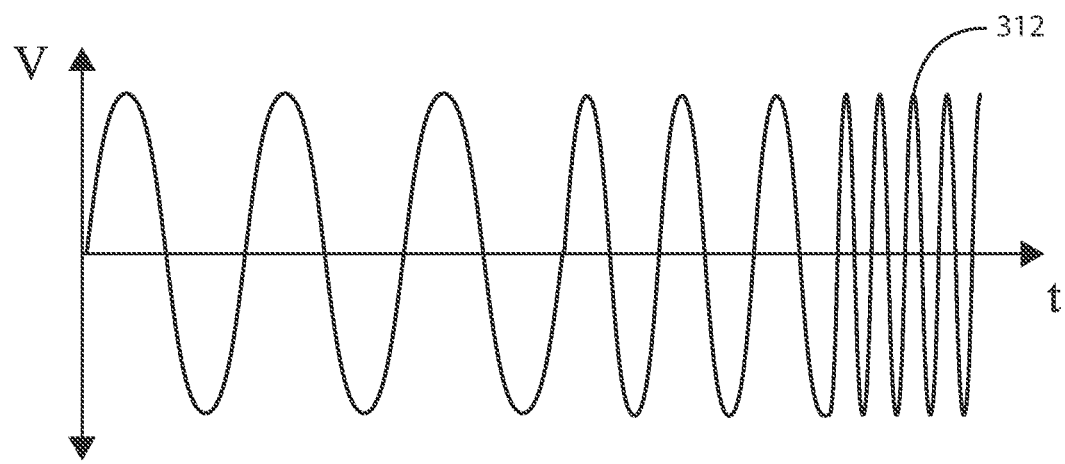
FIG. 3 is a plot of an exemplary therapy parameter in accordance with various embodiments herein.
Figure 4:
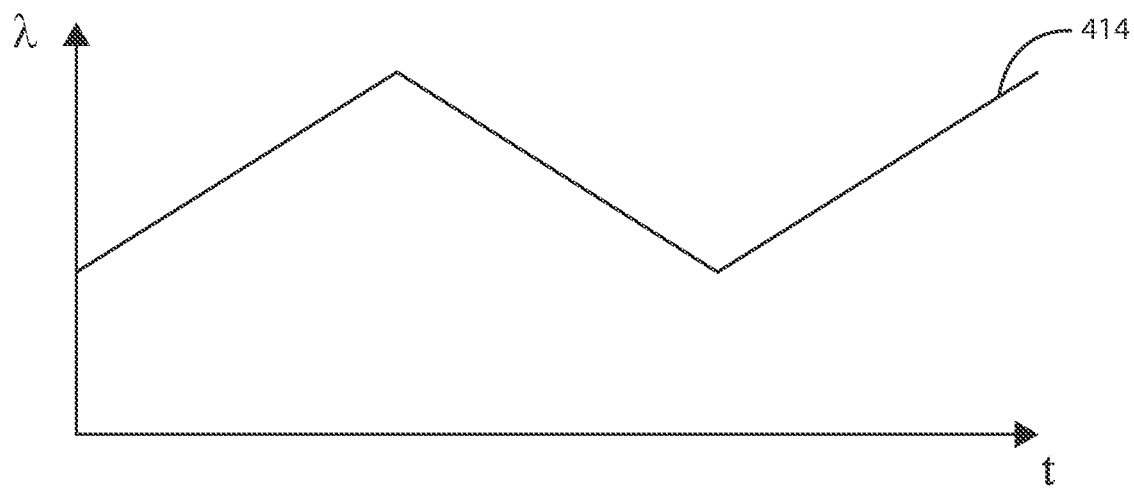
FIG. 4 is a plot of an exemplary therapy parameter in accordance with various embodiments herein.

In some embodiments, an electric field can be applied to the site of a cancerous tumor at a specific frequency or constant frequency range. However, in some embodiments, an electric field can be applied to the site of a cancerous tumor by sweeping through a range of frequencies. As one example, referring now to FIG. 3, exemplary plot 312 shows an alternating electric field, delivered by the electrodes 108, where the frequency increases over time. Similarly, FIG. 4 shows the change in frequency as a function of time in exemplary plot 414 during a programmed therapy parameter. In some embodiments, a frequency sweep can include sweeping from a minimum frequency up to a maximum frequency. In some embodiments, a frequency sweep can include sweeping from a maximum frequency down to a minimum frequency. In other embodiments, sweeping from a minimum frequency up to a maximum frequency and sweeping from the maximum frequency down to the minimum frequency can be repeated as many times as desired throughout the duration of the delivery of the electric field from the electric field generating circuit.

As therapy progresses during a frequency sweep, it may be desired to alternate between frequency ranges so that as the cells within a population change in size and number in response to therapy, more cells can be targeted. For example, in some embodiments, a frequency sweep can include alternating between a first frequency sweep covering a range of about 100 kHz to 300 kHz and a second frequency sweep covering a range about 200 kHz to 500 kHz. It will be appreciated that sweeping through a first and second frequency range as described can be performed indefinitely throughout the course of the therapy. In some embodiments, the second frequency sweep (range) can be at higher frequencies than the first frequency sweep (range). In some embodiments, the first frequency sweep (range) can be at higher frequencies than the second frequency sweep (range).

Frequency ranges for the first and second frequency ranges can be any range including specific frequencies recited above or below, provided that the lower end of each range is a value less than the upper end of each range. At times, it may be beneficial to have some amount of overlap between the frequency range of the first and second frequency sweep.

Medical Devices and Systems

Figure 5:
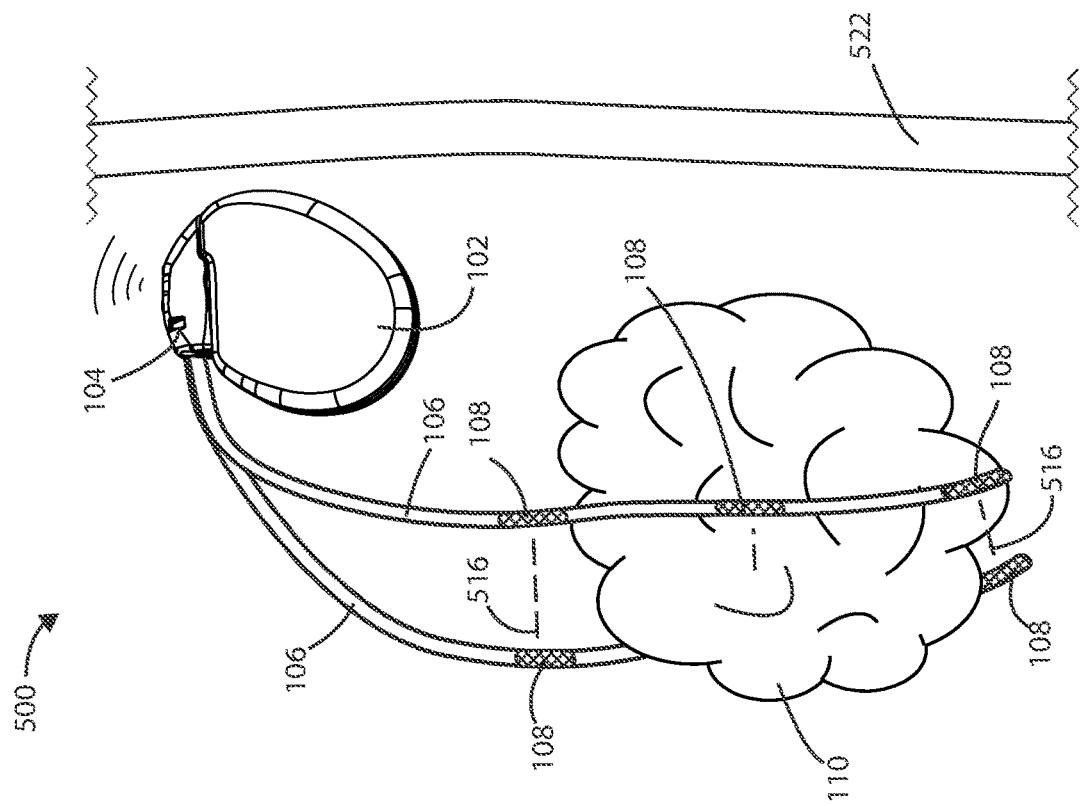
FIG. 5 is a schematic view of a medical device in accordance with various embodiments herein.

In reference now to FIG. 5, a schematic view of a medical device system for treating a cancerous tissue is shown. The medical device 500 can include housing 102, one or more leads 106, at least one electric field generating circuit, and control circuitry. The electric field generating circuit can be disposed within the housing 102. The electric field generating circuit can be configured to generate one or more electric fields. The control circuitry can be in communication with the electric field generating circuit. The control circuitry can be configured to control delivery of the one or more electric fields from the electric field generating circuit. The control circuitry can cause the electric field generating circuit to generate one or more electric fields, such as at frequencies selected from a range between 10 kHz to 1 MHz, as further discussed below.

The leads 106 can include one or more electrodes such as electrodes 108 disposed along the length of the leads 106. In various embodiments, the electrodes 108 can deliver the electric fields to the site of a tumor 110, such as a cancerous tumor, within the patient. In some embodiments, the electrodes 108 can include electric field generating electrodes and, in other embodiments, the electrodes 108 can include electric field sensing electrodes. In some embodiments, the leads 106 can include both electric field generating and electric field sensing electrodes. In various embodiments, at least one electrode 108 is configured to be implanted within the patient. In various embodiments, one or more leads 106 can be implanted leads. In various embodiments, one or more electrodes 108 can be implanted electrodes. In some embodiments, at least two electrodes 108 are configured to be implanted electrodes.

The proximal ends (or plugs) of leads 106 can be disposed within the header 104. The distal ends of electrical leads 106 can surround a tumor 110 such that the electrodes 108 are brought into proximity of the tumor 110. In some embodiments, the leads 106 can be positioned within the vasculature such that electrodes 108 are adjacent to or positioned within the tumor 110. However, it will be appreciated that leads 106 can be disposed in various places within or around the tumor 110. In some embodiments, the leads 106 can pass directly through the tumor 110.

In some embodiments, the leads 106 can include one or more tracking markers along the length of the lead for use in determining the precise location of the electrodes relative to the tumor. In some embodiments, the one or more tracking markers can be disposed directly distal or directly proximal to the one or more electrodes disposed on the lead. In some embodiments, the tracking markers can be formed from a magnetic material. In some embodiments, the tracking markers can be formed from a radiographic material. In some embodiments, the tracking markers can be formed from a fluorographic material.

It will be appreciated that a plurality of electric field vectors can be utilized between various combinations of electrodes 108 disposed along leads 106 to create an electric field. For example, one or more electric field vectors 516 can be generated between the most proximal electrodes 108 on the two leads 106. Similarly, one or more electric field vectors 516 can be generated between the distal most electrodes 108 on the two leads 106. It will also be appreciated that one or more electric field vectors can be generated between any combination of electrodes 108. In some embodiments, one or more electric field vectors can be generated between any combination of electrodes 108 and the housing 102 of the medical device 500.

It will be appreciated that one or more unipolar or multipolar leads can be used in accordance with the embodiments herein. In some embodiments, a combination of unipolar and multipolar leads can be used. In other embodiments, a circular lead, clamp lead, cuff lead, paddle lead, or patch lead can be used.

In some embodiments, a lead 106 can be a transcutaneous lead 106, such as a lead that extends through or across the skin 522 of the patient. The tissue designated by reference number 522 can include one or more of the epidermis, dermis, hypodermis, and/or other tissue beneath those layers. The implanted electrodes 108 can be disposed on a transcutaneous lead 106.

Leads

Figure 6:
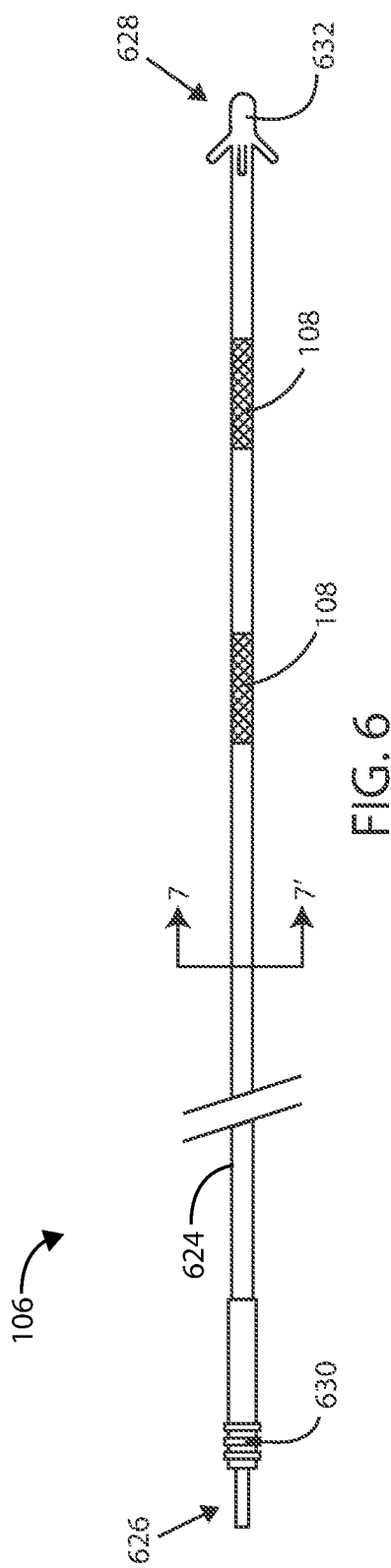
FIG. 6 is a schematic view of a lead in accordance with various embodiments herein.

Referring now to FIG. 6, a schematic view of a lead 106 is shown in accordance with various embodiments. The lead 106 can include a lead body 624 with a proximal end 626 and a distal end 628. In various embodiments, one or more electrodes 108 can be coupled to the lead body 624. The lead 106 can include one or more electrodes 108 positioned near the distal end 628. The electrode 108 can include various conductive materials such as platinum, silver, gold, iridium, titanium, and various alloys. In some embodiments, the lead 106 includes more than two electrodes 108.

The lead 106 can further include a terminal pin 630 for connecting the lead 106 to an implantable device, such as a cancer treatment device. The terminal pin 630 can be compatible with various standards for lead-header interface design including the DF-1, VS-1, IS-1, LV-1 and IS-4 standards, amongst other standards.

In some embodiments, the lead 106 can further include a fixation element 632, such as an element that can adhere to a portion of the patient's body to maintain the position of the lead 106 and/or the electrodes 108, in various embodiments, the fixation element 632 can be disposed along the distal end 628 of the lead 106.

Figure 7:
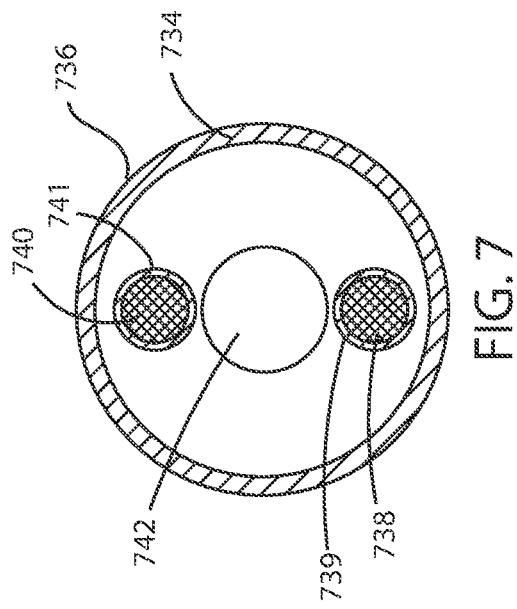
FIG. 7 is a cross-sectional view of the lead in FIG. 6 in accordance with various embodiments herein.

FIG. 7 shows a cross-sectional schematic view of a lead 106 as taken along line 7-7' of FIG. 6. The lead 106 can include an outer layer 734 with an outer surface 736. The outer layer 734 can be flexible and can be configured to protect other components disposed within the lumen of the outer layer 734. In some embodiments, the outer layer 734 can be circular in cross-section. In some embodiments, the outer layer 734 includes a dielectric material. In some embodiments, the outer layer 734 can include various biocompatible materials such as polysiloxanes, polyethylenes, polyamides, polyurethane and the like.

In various embodiments, the lead 106 can include one or more conductors 738, 740. In some embodiments, the first conductor 738 and the second conductor 740 can be disposed within the lumen of the outer layer 734. The conductors 738, 740 can be configured to provide electrical communication between an electrode 108 and the proximal end 626 of the lead 106. The conductors 738, 740 can include various materials including copper, aluminum, silver, gold, and various alloys such as tantalum/platinum, MP35N and the like. An insulator 739, 741 can surround the conductor 738, 740. The insulator 739, 741 can include various materials such as electrically insulating polymers (such as expanded polytetrafluoroethylene (ePTFE)).

In some embodiments, each of the electrodes 108 can have an individual conductor 738, 740 to electrically couple the electrode 108 to the proximal end 626 of the lead 106. In some embodiments, the conductor 738, 740 can be configured as a coil or a cable. Multiple conductors 738, 740 can be disposed within the lumen of the outer layer 734. For example, a separate conductor can be in communication with each electrode disposed on the lead. In various embodiments, an electrical conductor 738, 740 can form a part of an electrical circuit by which the electric fields from the electric field generating circuit are delivered to the site of the cancerous tissue. Many more conductors than are shown in FIG. 7 can be included within embodiments herein. For example, the lead 106 can include 1, 2, 3, 4, 5, 6, 7, 8, 10, 15 or 20 or more conductors, or a number of conductors falling within a range between any of the foregoing.

In some embodiments, the lead 106 can include a central channel 742. The central channel 742 can be configured for a guide wire, or other implanting device, to pass through, such as to aid in implanting the lead 106 and electrodes 108. In some cases, additional channels are disposed within the lead 106.

Electrodes

In reference now to FIG. 8, a cross-sectional schematic view of an electrode 108 is shown in accordance with various embodiments disclosed herein. FIGS. 8-13 and 15-18 show cross-sectional views of the distal most electrode 108. It should be noted that the disclosures of electrodes 108 can refer to distal most electrodes, proximal most electrodes, or any electrodes 108 disposed between. Electrodes 108 that are not the distal most can include one or more additional conductors 738, 740 extending through the lead body 624 and past the electrode 108, such as to electrically couple the more distal electrodes 108 to the proximal end 626 of the lead 106.

In some embodiments, the electrode 108 can include a plurality of conductive coil filars 844. The filars 844 can be formed of a conductive material (such as a conductive metal). In some cases the filars 844 can be clad with a conductive material that resists degradation such as platinum or a platinum alloy, iridium or an iridium alloy, or the like. The filars 844 can be disposed around the lead body 624. In some embodiments, the conductive coil filars 844 can include a first plurality of filars 846 and a second plurality of filars 848. In various embodiments, the first plurality of filars 846 can be in electrical communication with the second plurality of filars 848. In some embodiments, each of the filars 846 in the first plurality of filars 846 can be in electrical communication with the other filars 846 in the first plurality of filars 846. Similarly, in some embodiments, each of the filars 848 in the second plurality of filars 848 can be in electrical communication with the other filars 848 in the second plurality of filars 848. In some embodiments, a filar can contact another filar that is adjacent to the filar along the lengthwise axis of the lead body. Some filars, such as the inner filars, can contact two adjacent filars. End filars can contact one filar, such as an inner filar.

The first plurality of filars 846 can have a first diameter 847, and the second plurality of filars 848 can have a second diameter 849. In some embodiments, the second outer diameter 849 can be greater than the first outer diameter 847, such that the second plurality of filars 848 overlap with the first plurality of filars 846 along a lengthwise axis of the lead body 624. In some embodiments, a second inner diameter of the second plurality of filars 848 can be equal to the first outer diameter 847 of the first plurality of filars 846.

In various embodiments, the second plurality of filars 848 is separated from the outer surface 736 of the lead 106 by the first plurality of filars 846. In some embodiments, the second plurality of filars 848 is separated from the outer surface 736 of the lead 106 by a distance that is at least the diameter of a filars of the first plurality of filars 846. In some embodiments, the first plurality of filars 846 is disposed between the outer surface 736 of the lead 106 and the second plurality of filars 848.

In reference now to FIG. 9, a cross-sectional schematic view of an electrode 108 is shown in accordance with various embodiments disclosed herein. The electrode 108 can include a plurality of conductive coil filars 950 disposed around the lead body 624. In some embodiments, the conductive coil filars 950 can include a pitch 952 between successive or adjacent filars, such that adjacent filars do not contact each other along the lengthwise axis of the lead body 624. In some embodiments, the pitch 952 can be greater than or equal to half of the fiber diameter 954 of the conductive coil filars 950. In some embodiments, the pitch 952 can be greater than or equal to the fiber diameter 954 of the conductive coil filars 950. In some embodiments, the pitch 952 can be at least twice the fiber diameter 954. In some embodiments, the pitch 952 can be at least three times the fiber diameter 954. In some embodiments, the pitch 952 can be at least four times the fiber diameter 954. In some embodiments, the pitch 952 can be at least five times the fiber diameter 954. In some embodiments, the pitch 952 can be at least ten times the fiber diameter 954.

Figure 10:
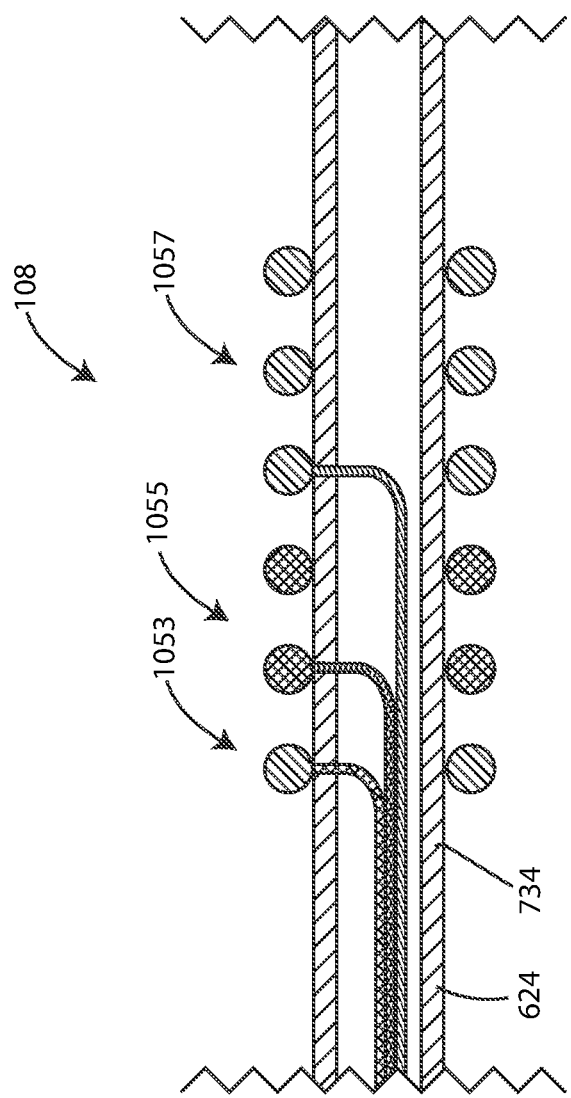
FIG. 10 is a cross-sectional schematic view of an electrode in accordance with various embodiments herein.

In reference now to FIG. 10, a cross-sectional schematic view of an electrode 108 is shown in accordance with various embodiments disclosed herein. The electrode 108 can include a plurality of segments 1053, 1055, 1057. In some embodiments, the electrode 108 can include two segments, three segments, four segments, five segments, or more. In various embodiments, each of the segments 1053, 1055, 1057 can be independently operated, such as each segment 1053, 1055, 1057 being configured to be producing an electric field or not producing an electric field regardless of the status of the other segments 1053, 1055, 1057. In some embodiments, each of the segments 1053, 1055, 1057 can be of equivalent size and/or shape. In other embodiments, the segments 1053, 1055, 1057 can differ in size and/or shape, such as shown in FIG. 10.

Figure 11:
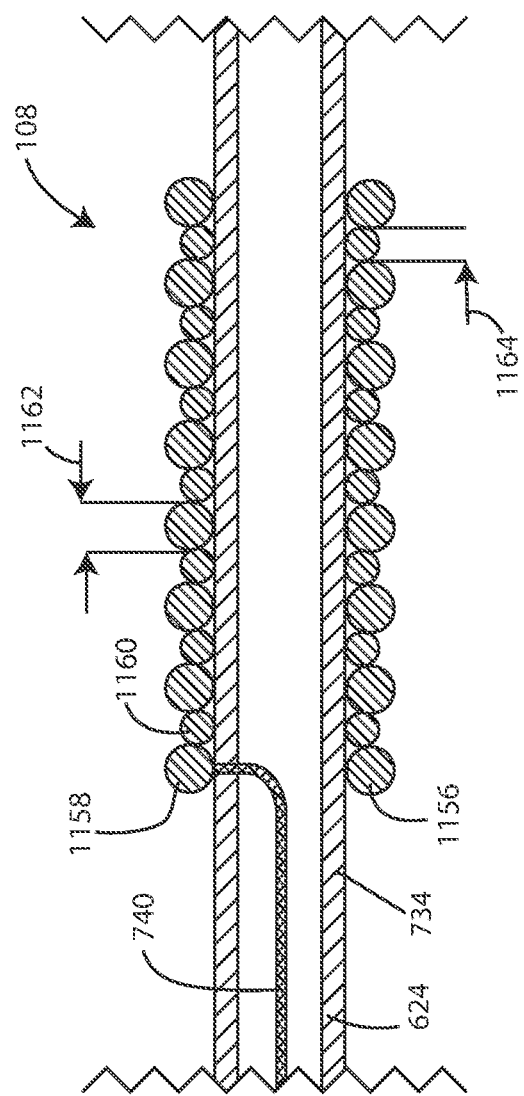
FIG. 11 is a cross-sectional schematic view of an electrode in accordance with various embodiments herein.

In reference now to FIG. 11, a cross-sectional schematic view of an electrode 108 is shown in accordance with various embodiments disclosed herein. The electrode 108 can include a plurality of conductive coil filars 1156 disposed around the lead body 624. In some embodiments, the plurality of conductive coil filars 1156 can include a first plurality of filars 1158 and a second plurality of filars 1160. In some embodiments, the first plurality of filars 1158 can have a first fiber diameter 1162, and the second plurality of filars 1160 can have a second fiber diameter 1164. In various embodiments, the first fiber diameter 1162 can be greater than the second fiber diameter 1164. In some embodiments, the electrode 108 can include alternating first filars 1158 and second filars 1160.

In various embodiments, the first fiber diameter 1162 can be at least 1.5 times the size of the second fiber diameter 1164. In various embodiments, the first fiber diameter 1162 can be at least twice the size of the second fiber diameter 1164. In various embodiments, the first fiber diameter 1162 can be at least three times the size of the second fiber diameter 1164. In various embodiments, the first fiber diameter 1162 can be at least four times the size of the second fiber diameter 1164. In various embodiments, the first fiber diameter 1162 can be at least five times the size of the second fiber diameter 1164.

Increased Surface Area on Electrodes

Figure 12:
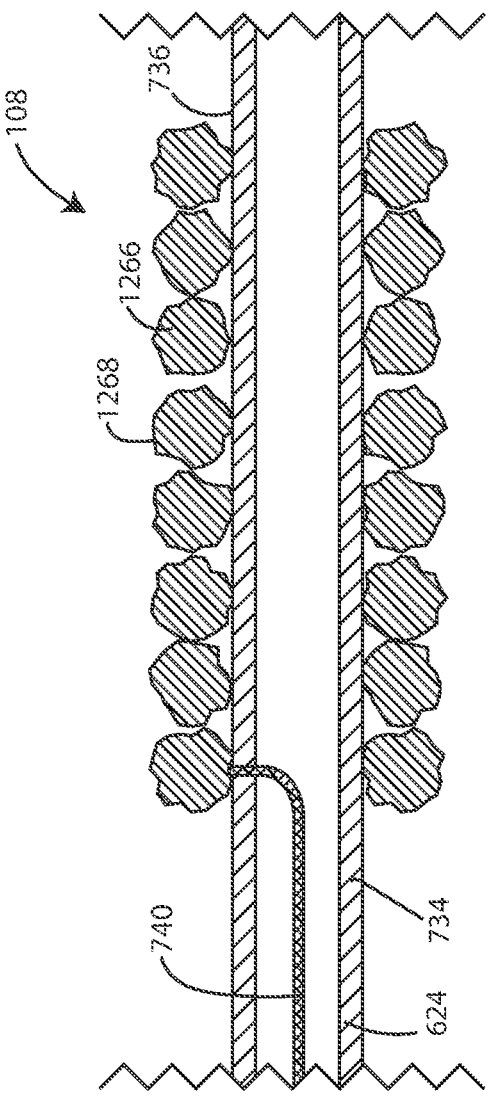
FIG. 12 is a cross-sectional schematic view of an electrode in accordance with various embodiments herein.
Figure 13:
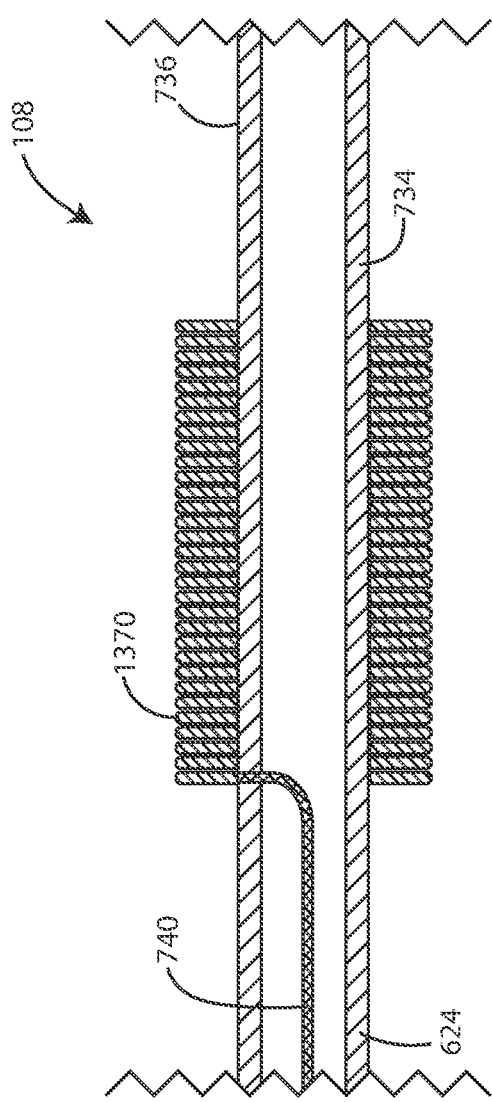
FIG. 13 is a cross-sectional schematic view of an electrode in accordance with various embodiments herein.

In reference now to FIG. 12, a cross-sectional schematic view of an electrode 108 is shown in accordance with various embodiments disclosed herein. The electrode 108 can include a plurality of conductive coil filars 1266 disposed around the lead body 624. In some embodiments, the conductive coil filars 1266 can include an irregular surface 1268 with increased surface area compared with otherwise identical conductive coil filars having a substantially smooth surface, such as those shown in FIG. 8-11. By way of example, the surface area can be increased based on having a rough and/or irregular surface such that the surface area is at least 5, 10, 15, 20, 25, 30, 40, 50, 75, 100, 200, 300, 400, 500, 750, or 1000 percent greater than a perfectly circular filar having the same diameter for a given length (wherein the surface area of a perfectly circular filar can be calculated according to the equation "Surface Area=$2\pi rl$", wherein r is the radius of the filar and l is the length of the filar).

In some embodiments, the irregular surface 1268 can be a result of a surface finishing process. In some embodiments, the irregular surface 1268 can be an etched surface, such as a chemical etched surface. In some embodiments, the irregular surface 1268 can be a cut surface, such as a laser-cut surface. In some embodiments, the irregular surface 1268 can be a result of a manufacturing process of the filars 1266, such as stamping or extruding the filars 1266 with an irregular surface. In some embodiments, the irregular surface 1268 can be a result of a treatment, such as iridium oxide.

Conductive Pillars

In some embodiments, the surface of the electrode can be formed using a plurality of conductive pillars. In reference now to FIG. 13, a cross-sectional schematic view of an electrode 108 is shown in accordance with various embodiments disclosed herein. The electrode 108 can include a plurality of conductive pillars 1370 disposed around the lead body 624. In some embodiments, each conductive pillar 1370 can be roughly cylindrical or have a roughly circular cross-section. In some embodiments, one or more of the conductive pillars 1370 can extend around the lead body 624, such as to provide a fin-like shape. In various embodiments, the conductive pillars 1370 can be tantalum pillars. However, many other conductors (and specifically metals) can be used herein to form pillars. Various techniques can be used to form the conductive pillars including, but not limited to, sputtering techniques, etching techniques, additive manufacturing techniques, and the like.

Expanding Elements

Various embodiments can include an expanding element, such as an expanding electrode or a stent. An expanding element can be configured to be delivered to a desired location in a compressed or unexpanded state. An expanding element can be delivered in a compressed state such as to allow the expanding element to pass through areas which would otherwise be too small for the expanding element to pass through. In other embodiments, the expanding element can be delivered in a compressed state to allow flow, such as flow of blood, past the expanding element as the expanding element is delivered to its desired location. In some embodiments, an expanding element can be a self-expanding element, such as an element that automatically expands, such as by removal of a delivery sheath or catheter. In some embodiments, an expanding element can be formed a shape-memory material, such as a shape-memory metal (such as the nickel-titanium alloy nitinol) or a shape-memory polymer. In some embodiments, an expanding element can require an input to expand, such as a balloon-like expanding element.

Figure 14:
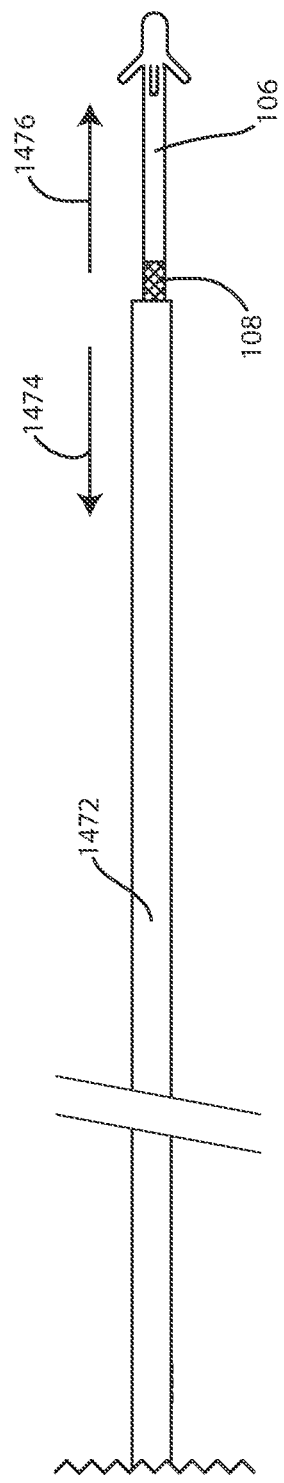
FIG. 14 is a schematic view of a lead and a delivery device in accordance with various embodiments herein.

In reference now to FIG. 14, a schematic view of a lead 106 and a delivery device 1472 are shown in accordance with various embodiments disclosed herein. In some embodiments, the medical device system can include a delivery device 1472, such as a delivery catheter or a delivery sheath. The lead 106 can be inserted into the patient within the delivery device 1472.

Upon reaching an intended location within the patient, the lead 106 can be at least partially removed from the delivery device 1472. In some embodiments, the lead 106 can be removed from the delivery device 1472 by withdrawing the delivery device 1472 in the direction of arrow 1474 while the lead 106 remains stationary. In some embodiments, the lead 106 can be removed from the delivery device 1472 by further inserting the lead 106 in the direction of arrow 1476 while the delivery device 1472 remains stationary. In other embodiments, the lead 106 can be removed from the delivery device 1472 by a combination of further inserting the lead 106 in the direction of arrow 1476 and withdrawing the delivery device 1472 in the direction of arrow 1474. In some embodiments, once the electrode 108 has been removed from within the delivery device 1472 the electrode 108 can expand into an expanded state.

Figure 15:
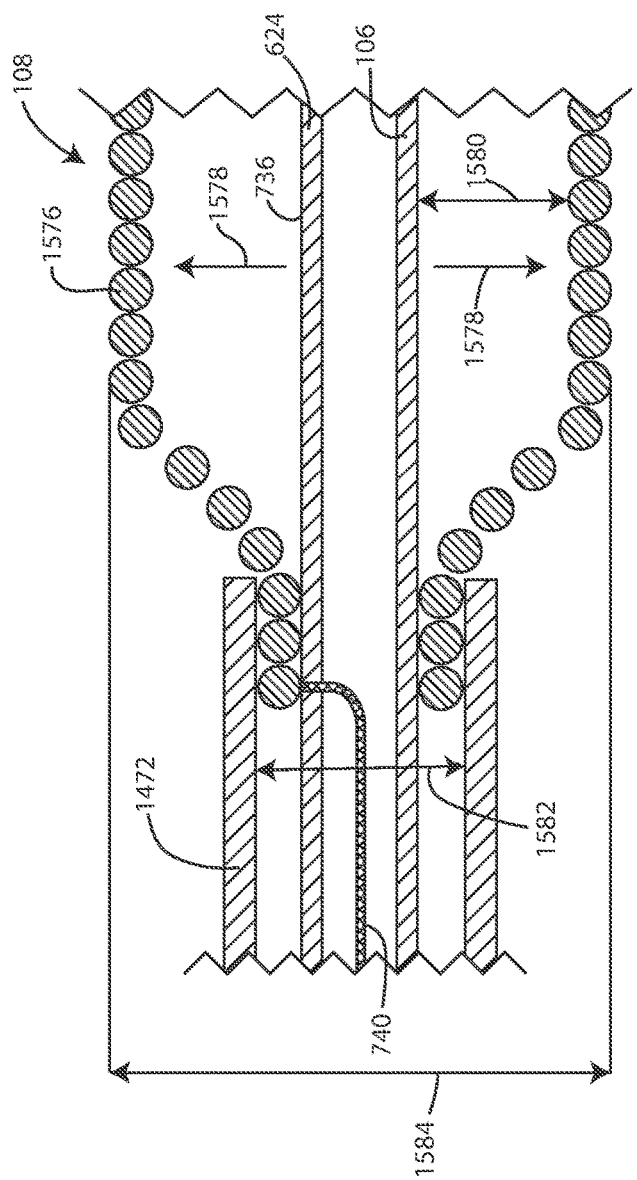
FIG. 15 is a cross-sectional schematic view of an electrode in accordance with various embodiments herein.

In reference now to FIG. 15, a cross-sectional schematic view of an electrode 108 is shown in accordance with various embodiments disclosed herein. The electrode 108 can include a plurality of conductive coil filars 1576 disposed around the lead body 624. In some embodiments, the conductive coil filars 1576 can be configured to expand in outer diameter, shown by arrow 1578, after removal of the delivery device 1472. From over the conductive coil filars 1576. The conductive coil filars 1576 can expand from a first outer diameter 1582 to a second outer diameter 1584, such that the second outer diameter 1584 is larger than the first outer diameter 1582. In some embodiments, the second outer diameter 1584 can be at least twice the size of the first outer diameter 1582. In some embodiments, the second outer diameter 1584 can be at least three times the size of the first outer diameter 1582. In some embodiments, the second outer diameter 1584 can be at least four times the size of the first outer diameter 1582.

In various embodiments, in the compressed state, the conductive coil filars 1576 can be adjacent to or can contact the outer surface 736. In various embodiments, in the expanded state, a gap 1580 can separate at least some of the plurality of conductive coil filars 1576 from the outer surface 736.

Coatings

Figure 16:
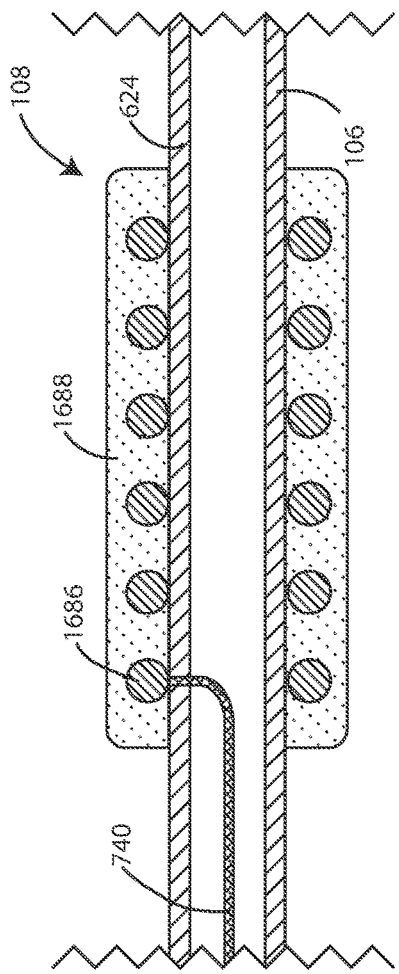
FIG. 16 is a cross-sectional schematic view of an electrode in accordance with various embodiments herein.

In reference now to FIG. 16, a cross-sectional schematic view of an electrode is shown in accordance with various embodiments disclosed herein. In various embodiments, the medical device systems disclosed herein can include a material 1688 disposed over the conductive coil filars 1686. In some embodiments, the material 1688 can be a conductive material, such as a conductive fluid or gel. As a conductive material, the electric field generated by the electrode 108 can pass through the material 1688. In some embodiments, the material 1688 can cover all of the conductive coil filars 1686. In some embodiments, the material 1688 covers a portion of the conductive coil filars 1686, such as at least 75% of the conductive coil filars 1686, at least 50% of the conductive coil filars 1686, or at least 25% of the conductive coil filars 1686.

In some embodiments, the material 1688 can be an active agent (or drug) and/or the material 1688 can include an active agent disposed therein. In various embodiments, the active agent can include a chemotherapeutic agent, such as an agent to further treat the cancerous tissue. In various embodiments, the active agent can include an anti-bacterial agent, such as to treat an infection or prevent an infection.

In reference now to FIG. 17 a cross-sectional schematic view of an electrode 108 is shown in accordance with various embodiments disclosed herein. In some embodiments, the medical device system can further include a layer of material 1790 disposed over the conductive coil filars 1792. In various embodiments, the material 1790 can be configured to prevent the ingrowth of tissue into the area around the conductive coil filars 1792. In some embodiments, the material 1790 can include an expanded (porous) polytetrafluoroethylene ("PTFE") film (such as GORE-TEX®). In various embodiments, the material 1790 can be electrically conductive, so as to allow the flow of a current there across. In various embodiments, the material 1790 can be porous to small molecules such as small ionic molecules including metal cations (sodium, potassium, calcium, etc.). In various embodiments, the material 1790 is not porous to proteins, cellular structures, and the like such as to prevent ingrowth of tissue into the area around the conductive coil filars 1792. In other embodiments, the material 1790 can be configured to promote ingrowth of tissue, such as to aid in fixation of the electrodes in desired location or to reduce surface impedance.

Electrode Past Distal End of Lead

In reference now to FIG. 18 a cross-section schematic view of an electrode 108 is shown in accordance with various embodiments disclosed herein. In various embodiments, the electrode 108 can extend longitudinally beyond the distal end 628 of the lead body 624. For example, the electrode 108 can extend at least 0.1, 0.2, 0.3, 0.4, 0.5, 0.75, 1, 1.5, 2, 2.5, 3, 4 or 5 centimeters beyond the distal end 628 of the lead body (or an amount falling within a range between any of the foregoing). In some embodiments, the proximal most conductive coil filars 1894 can be disposed more proximal than the distal end 628 of the lead body 624. In various embodiments, the electrode 108 can define an open lumen 1896, such that at least a portion of the lumen, such as the distal most portion of the lumen, formed by the conductive coil filars 1894 is not occupied by the lead body 624.

Stents and Electrodes

Figure 19:
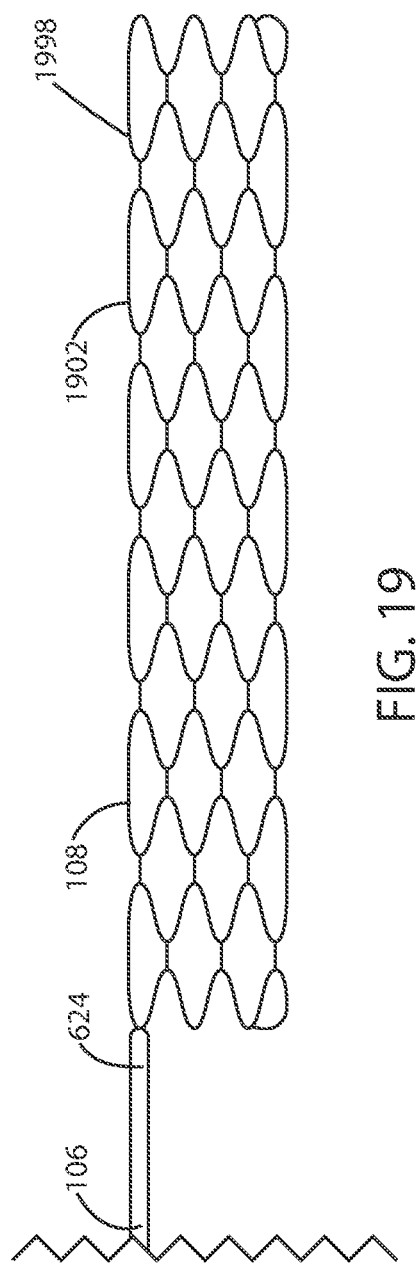
FIG. 19 is a schematic view of a stent in accordance with various embodiments herein.

In reference now to FIG. 19 a cross-section schematic view of a stent 1998 is shown in accordance with various embodiments disclosed herein. In some embodiments, a stent 1998 can be coupled to a distal portion of the lead body 624. In some embodiments, the stent 1998 can include a stent frame 1902. The stent frame 1902 can be substantially cylindrical defining an open lumen. In some embodiments, the stent frame 1902 is expandable from a first diameter to a second larger diameter. Expansion from the first diameter to the second diameter can be associated with deployment of the stent within a desired area of the vasculature or other bodily structures. In various embodiments, the stent frame 1902 can be formed of an electrically conductive material. In various embodiments, the stent frame 1902 can serve as an electrode 108, such as the distal most electrode. As such, in some embodiments, the stent frame 1902 can be in electrical contact with one or more conductors within the lead body.

In various embodiments, the stent 1998 can include a bioerodible material, such as a material that erodes in response to exposure to the in vivo environment. In some embodiments, the stent 1998 can include a bioerodible metal, such as a bioerodible magnesium alloy. Exemplary bioerodible metals and alloys are described in U.S. Pat. No. 8,002,821, the content of which is herein incorporated by reference.

Figure 20:
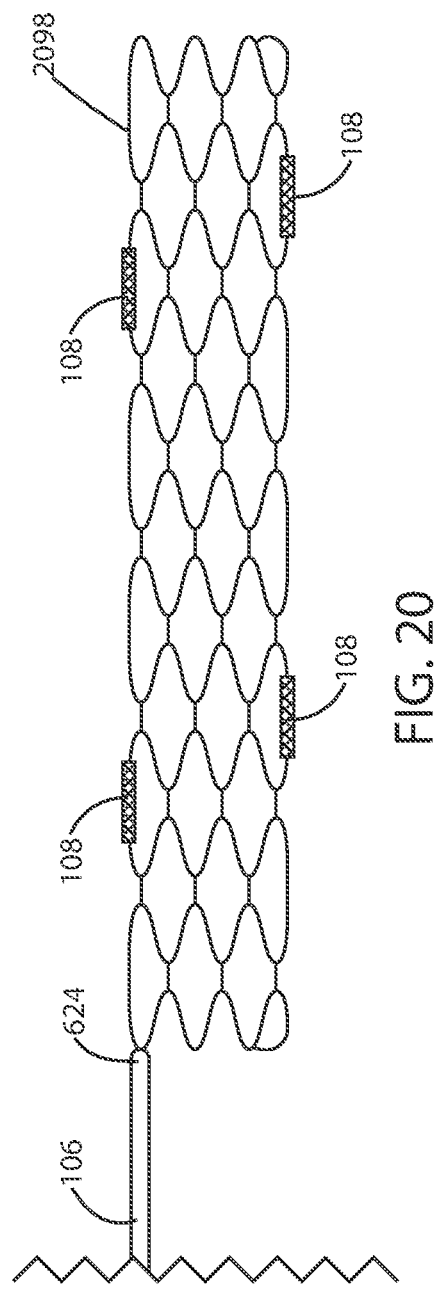
FIG. 20 is a schematic view of a stent with electrodes in accordance with various embodiments herein.

In some cases, such as where a stent frame itself does not serve as an electrode, one or more electrodes (and/or conductors to provide electrical communication) can be mounted on the stent frame. By way of example, in reference now to FIG. 20, a schematic view of a stent 2098 with electrodes 108 is shown in accordance with various embodiments disclosed herein. In various embodiments, a stent 2098 can be coupled to the lead body 624 at a distal portion thereof, such as at the distal end 628. In some embodiments, an electrode 108 can be disposed on an outside surface of the stent 2098. In some embodiments, a plurality of electrodes 108 can be disposed on an outside surface of the stent 2098. In some cases, the stent can be formed of a bioerodible material such that it is useful for initial positioning of the electrodes but it erodes away leaving the electrodes (and associated conductors) in place.

In some embodiments, the stent 2098 can be a rigid stent, such as a stent that does not expand or contract. The stent 2098 can include a rigid biliary or pancreatic style stent, such as a plastic tube-like structure. The stent 2098 can also include one or more barbs to hold the stent in place.

Figure 21:
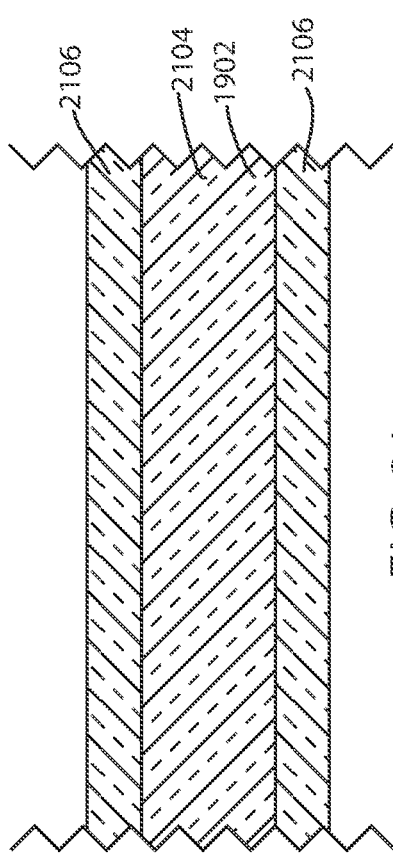
FIG. 21 is a cross-sectional schematic view of a portion of a stent in accordance with various embodiments herein.

In reference now to FIG. 21, a cross-sectional schematic view of a portion of a stent frame 1902 is shown in accordance with various embodiments disclosed herein. In various embodiments, a stent can include a stent frame 1902. The stent frame 1902 can be formed of an electrically conductive material 2104 including metals, metal alloys, and the like. In various embodiments, the stent frame 1902 can be coated or clad for stability. In some embodiment embodiments, the stent frame 1902 can be clad with a material 2106 resistant to degradation as a result of exposure to electrical currents, such as the electrical currents used to generate the electric fields. For example, the stent frame 1902 can be clad with platinum or platinum alloys, iridium or iridium alloys, and the like.

Figure 22:
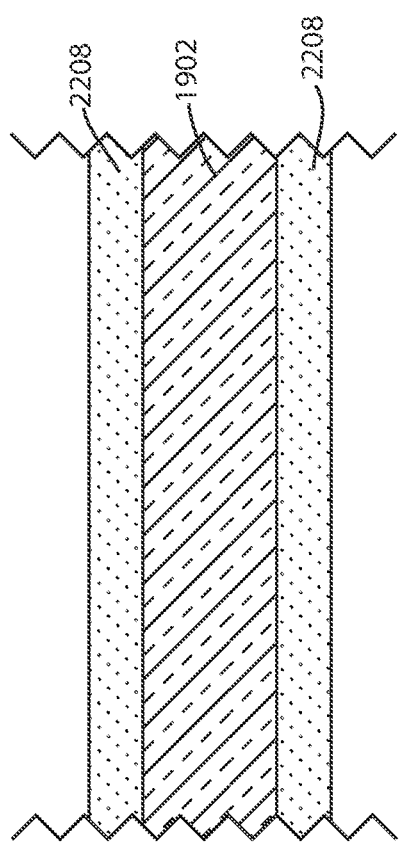
FIG. 22 is a cross-sectional schematic view of a portion of a stent in accordance with various embodiments herein.

In reference now to FIG. 22, a cross-sectional schematic view of a portion of a stent frame 1902 is shown in accordance with various embodiments disclosed herein. In various embodiments, the stent frame 1902 can be coated with a conductive fluid or gel 2208, such as to allow electric field to pass through the conductive fluid or gel 2208. In some embodiments, an active agent can be disposed within the conductive fluid or gel 2208. In various embodiments the active agent can include chemotherapeutic agent or an anti-bacterial agent.

Medical Device Components

Figure 23:
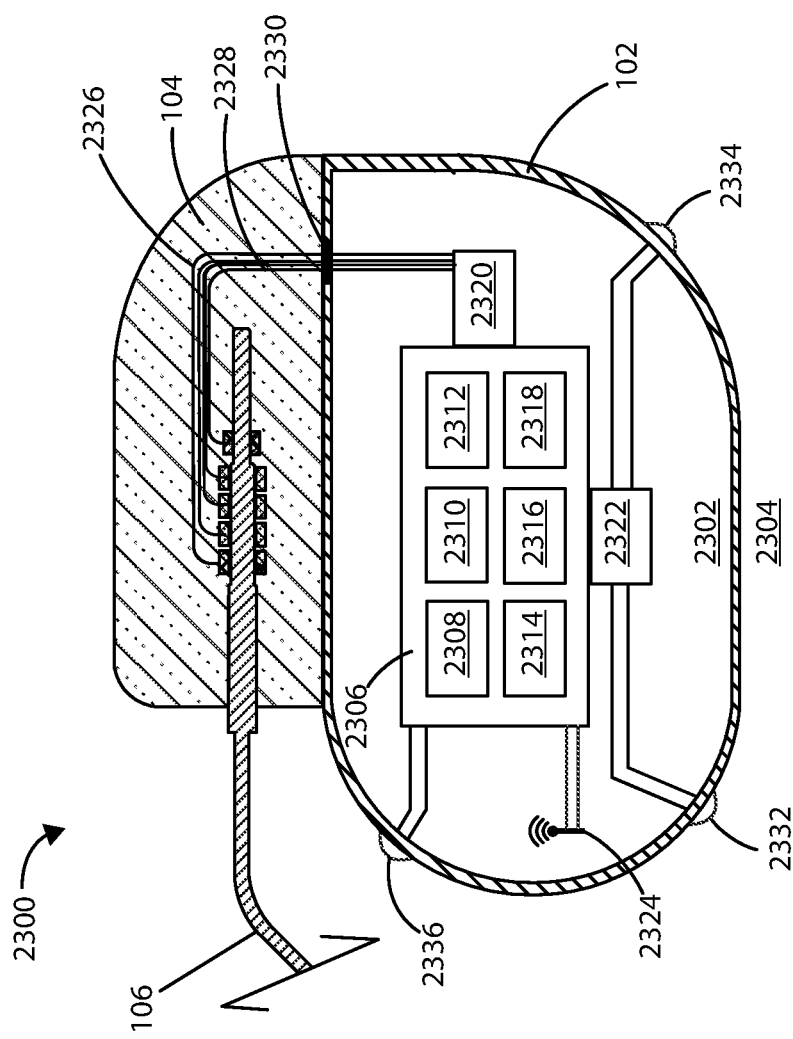
FIG. 23 is a schematic cross-sectional view of a medical device in accordance with various embodiments herein.

Referring now to FIG. 23, a schematic cross-sectional view of medical device 2300 is shown in accordance with various embodiments herein. The housing 102 can define an interior volume 2302 that can be hollow and that in some embodiments is hermetically sealed off from the area 2304 outside of medical device 2300. In other embodiments the housing 102 can be filled with components and/or structural materials such that it is non-hollow. The medical device 2300 can include control circuitry 2306, which can include various components 2308, 2310, 2312, 2314, 2316, and 2318 disposed within housing 102. In some embodiments, these components can be integrated and in other embodiments these components can be separate. In yet other embodiments, there can be a combination of both integrated and separate components. The medical device 2300 can also include an antenna 2324, to allow for unidirectional or bidirectional wireless data communication, such as with an external device or an external power supply. In some embodiments, the components of medical device 2300 can include an inductive energy receiver coil (not shown) communicatively coupled or attached thereto to facilitate transcutaneous recharging of the medical device via recharging circuitry.

The various components 2308, 2310, 2312, 2314, 2316, and 2318 of control circuitry 2306 can include, but are not limited to, a microprocessor, memory circuit (such as random access memory (RAM) and/or read only memory (ROM)), recorder circuitry, controller circuit, a telemetry circuit, a power supply circuit (such as a battery), a timing circuit, and an application specific integrated circuit (ASIC), a recharging circuit, amongst others. Control circuitry 2306 can be in communication with an electric field generating circuit 2320 that can be configured to generate electric current to create one or more fields. The electric field generating circuit 2320 can be integrated with the control circuitry 2306 or can be a separate component from control circuitry 2306. Control circuitry 2306 can be configured to control delivery of electric current from the electric field generating circuit 2320. In some embodiments, the electric field generating circuit 2320 can be present in a portion of the medical device that is external to the body.

In some embodiments, the control circuitry 2306 can be configured to direct the electric field generating circuit 2320 to deliver an electric field via leads 106 to the site of a cancerous tumor located within a bodily tissue. In other embodiments, the control circuitry 2306 can be configured to direct the electric field generating circuit 2320 to deliver an electric field via the housing 102 of medical device 2300 to the site of a cancerous tumor located within a bodily tissue. In other embodiments, the control circuitry 2306 can be configured to direct the electric field generating circuit 2320 to deliver an electric field between leads 106 and the housing 102 of medical device 2300. In some embodiments, one or more leads 106 can be in electrical communication with the electric field generating circuit 2320.

In some embodiments, various components within medical device 2300 can include an electric field sensing circuit 2322 configured to generate a signal corresponding to sensed electric fields. Electric field sensing circuit 2322 can be integrated with control circuitry 2306 or it can be separate from control circuitry 2306.

Sensing electrodes can be disposed on or adjacent to the housing of the medical device, on one or more leads connected to the housing, on a separate device implanted near or in the tumor, or any combination of these locations. In some embodiments, the electric field sensing circuit 2322 can include a first sensing electrode 2332 and a second sensing electrode 2334. In other embodiments, the housing 102 itself can serve as a sensing electrode for the electric field sensing circuit 2322. The electrodes 2332 and 2334 can be in communication with the electric field sensing circuit 2322. The electric field sensing circuit 2322 can measure the electrical potential difference (voltage) between the first electrode 2332 and the second electrode 2334. In some embodiments, the electric field sensing circuit 2322 can measure the electrical potential difference (voltage) between the first electrode 2332 or second electrode 2334, and an electrode disposed along the length of one or more leads 106. In some embodiments, the electric field sensing circuit can be configured to measure sensed electric fields and to record electric field strength in V/cm.

It will be appreciated that the electric field sensing circuit 2322 can additionally measure an electrical potential difference between the first electrode 2332 or the second electrode 2334 and the housing 102 itself. In other embodiments, the medical device can include a third electrode 2336, which can be an electric field sensing electrode or an electric field generating electrode. In some embodiments, one or more sensing electrodes can be disposed along lead 106 and can serve as additional locations for sensing an electric field. Many combinations can be imagined for measuring electrical potential difference between electrodes disposed along the length of one or more leads 106 and the housing 102 in accordance with the embodiments herein.

In some embodiments, the one or more leads 106 can be in electrical communication with the electric field generating circuit 2320. The one or more leads 106 can include one or more electrodes 108, as shown in FIGS. 1 and 2. In some embodiments, various electrical conductors, such as electrical conductors 2326 and 2328, can pass from the header 104 through a feed-through structure 2330 and into the interior volume 2302 of medical device 2300. As such, the electrical conductors 2326 and 2328 can serve to provide electrical communication between the one or more leads 106 and control circuitry 2306 disposed within the interior volume 2302 of the housing 102.

In some embodiments, recorder circuitry can be configured to record the data produced by the electric field sensing circuit 2322 and record time stamps regarding the same. In some embodiments, the control circuitry 2306 can be hardwired to execute various functions, while in other embodiments the control circuitry 2306 can be directed to implement instructions executing on a microprocessor or other external computation device. A telemetry circuit can also be provided for communicating with external computation devices such as a programmer, a home-based unit, and/or a mobile unit (e.g. a cellular phone, personal computer, smart phone, tablet computer, and the like).

Figure 24:
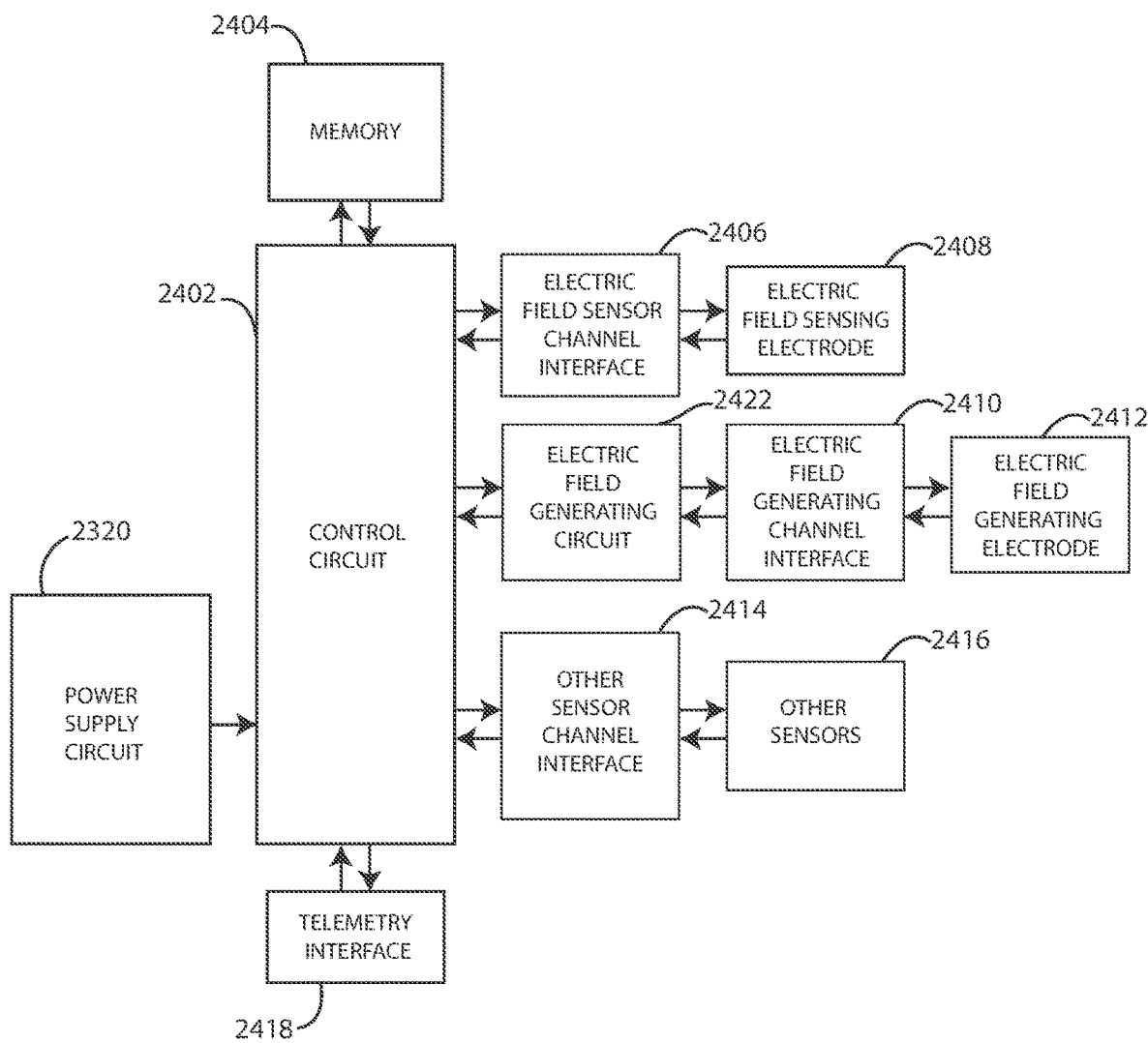
FIG. 24 is a schematic diagram of components of a medical device in accordance with various embodiments herein.

Elements of various embodiments of the medical devices described herein are shown in FIG. 24. However, it will be appreciated that some embodiments can include additional elements beyond those shown in FIG. 24. In addition, some embodiments may lack some elements shown in FIG. 24. The medical devices as embodied herein can gather information through one or more sensing channels and can output information through one or more field generating channels. A microprocessor 2402 can communicate with a memory 2404 via a bidirectional data bus. The memory 2404 can include read only memory (ROM) or random-access memory (RAM) for program storage and RAM for data storage. The microprocessor 2402 can also be connected to a telemetry interface 2418 for communicating with external devices such as a programmer, a home-based unit and/or a mobile unit (e.g. a cellular phone, personal computer, smart phone, tablet computer, and the like) or directly to the cloud or another communication network as facilitated by a cellular or other data communication network. The medical device can include a power supply circuit 2320. In some embodiments, the medical device can include an inductive energy receiver coil interface (not shown) communicatively coupled or attached thereto to facilitate transcutaneous recharging of the medical device.

The medical device can include one or more electric field sensing electrodes 2408 and one or more electric field sensor channel interfaces 2406 that can communicate with a port of microprocessor 2402. The medical device can also include one or more electric field generating circuits 2422, one or more electric field generating electrodes 2412, and one or more electric field generating channel interfaces 2410 that can communicate with a port of microprocessor 2402. The medical device can also include one or more physiological sensors, respiration sensors, or chemical sensors 2416 and one or more physiological/respiration/chemical sensor channel interfaces 2414 that can communicate with a port of microprocessor 2402. The channel interfaces 2406, 2410, and 2414 can include various components such as analog-to-digital converters for digitizing signal inputs, sensing amplifiers, registers which can be written to by the control circuitry in order to adjust the gain and threshold values for the sensing amplifiers, source drivers, modulators, demodulators, multiplexers, and the like.

In some embodiments, the physiological sensors can include sensors that monitor temperature, blood flow, blood pressure, and the like. In some embodiments, the respiration sensors can include sensors that monitor respiration rate, respiration peak amplitude, and the like. In some embodiments, the chemical sensors can measure the quantity of an analyte present in a treatment area about the sensor, including but not limited to analytes such as of blood urea nitrogen, creatinine, fibrin, fibrinogen, immunoglobulins, deoxyribonucleic acids, ribonucleic acids, potassium, sodium, chloride, calcium, magnesium, lithium, hydronium, hydrogen phosphate, bicarbonate, and the like. However, many other analytes are also contemplated herein. Exemplary chemical/analyte sensors are disclosed in commonly owned U.S. Pat. No. 7,809,441 to Kane et al., and which is hereby incorporated by reference in its entirety.

Although the physiological, respiration, or chemical sensors 2416 are shown as part of a medical device in FIG. 24, it is realized that in some embodiments one or more of the physiological, respiration, or chemical sensors could be physically separate from the medical device. In various embodiments, one or more of the physiological, respiration, or chemical sensors can be within another implanted medical device communicatively coupled to a medical device via telemetry interface 2418. In yet other embodiments, one or more of the physiological, respiration, or chemical sensors can be external to the body and coupled to a medical device via telemetry interface 2418.

Methods

Many different methods are contemplated herein, including, but not limited to, methods of making, methods of using, and the like. Aspects of system/device operation described elsewhere herein can be performed as operations of one or more methods in accordance with various embodiments herein.

Figure 25:
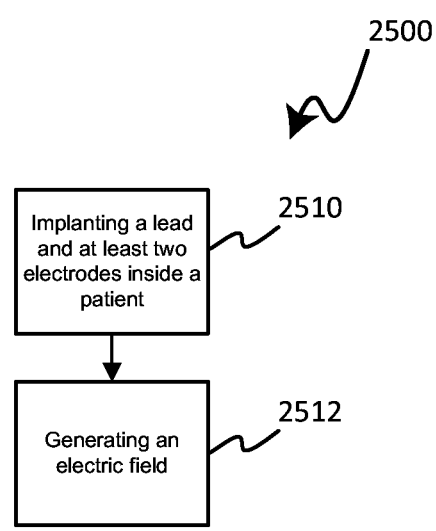
FIG. 25 is a flow chart depicting a method in accordance with various embodiments herein.

In reference now to FIG. 25, a method 2500 of treating a cancerous tumor is shown in accordance with various embodiments herein. In an embodiment, a method 2500 of treating a cancerous tumor is included, the method 2500 can include implanting a lead and at least two electrodes inside a body of a patient with the cancerous tumor, step 2510. The method 2500 can include generating an electrical field between at least one pair of electrodes, step 2512.

In various embodiments, the electric field can have frequencies within a range of between 10 kHz to 1 MHz. In some embodiments, the lead can include a lead body can include a proximal end and a distal end, the lead body can include a first electrical conductor disposed within the lead body; and a first electrode coupled to the lead body. In some embodiments, the first electrode can be in electrical communication with the first electrical conductor. In some embodiments, the first electrical conductor can form part of an electrical circuit by which the electric fields from the electric field generating circuit are delivered to the site of the cancerous tissue. In some embodiments, the first electrode can include a plurality of conductive coil filars disposed around the lead body. In some embodiments, the first electrode can include a plurality of conductive pillars disposed around the lead body.

MRI Artifact

Various embodiments provided herein can include an electrode which performs advantageously during imaging processes, such as during an MRI. In some embodiments, the electrode can be configured to not appear in an MRI, such as to not block portions of the patient's body that a clinician is attempting to view through an MRI. In some embodiments, the shape or the materials in the electrode can provide advantageous performance during imaging processes.

Electrical Stimulation Parameters

In various embodiments, systems or device herein (or components thereof, such as control circuitry) can be configured to direct an electric field generating circuit to deliver an electric field using one or more frequencies selected from a range of between 10 kHz to 1 MHz. In some embodiments, the control circuitry can be configured to direct the electric field generating circuit to deliver an electric field at one or more frequencies selected from a range of between 100 kHz to 500 kHz. In some embodiments, the control circuitry can be configured to direct the electric field generating circuit to deliver an electric field at one or more frequencies selected from a range of between 100 kHz to 300 kHz. In some embodiments, the control circuitry can be configured to direct the electric field generating circuit to periodically deliver an electric field using one or more frequencies greater than 1 MHz.

In some embodiments, the electric field can be effective in disrupting cellular mitosis in cancerous cells. The electric field can be delivered to the site of a cancerous tumor along more than one vector. In some examples, the electric field can be delivered along at least one vector, including at least one of the lead electrodes. In some embodiments, at least two vectors with spatial diversity between the two vectors can be used. The vectors can be spatially separated (e.g., the vectors can be disposed at an angle with respect to one another) by at least about 10, 20, 30, 40, 50, 60, 70, 80 or 90 degrees.

A desired electric field strength can be achieved by delivering an electric current between two electrodes. The specific current and voltage at which the electric field is delivered can vary and can be adjusted to achieve the desired electric field strength at the site of the tissue to be treated. In some embodiments, the control circuitry can be configured to direct the electric field generating circuit to deliver an electric field using currents ranging from 1 mAmp to 1000 mAmp to the site of a cancerous tumor. In some embodiments, the control circuitry can be configured to direct the electric field generating circuit to deliver an electric field using currents ranging from 20 mAmp to 500 mAmp to the site of a cancerous tumor. In some embodiments, the control circuitry can be configured to direct the electric field generating circuit to deliver an electric field using currents ranging from 30 mAmp to 300 mAmp to the site of a cancerous tumor.

In some embodiments, the control circuitry can be configured to direct the electric field generating circuit to deliver an electric field using currents including 1 mAmp, 2 mAmp, 3 mAmp, 4 mAmp, 5 mAmp, 6 mAmp, 7 mAmp, 8 mAmp, 9 mAmp, 10 mAmp, 15 mAmp, 20 mAmp, 25 mAmp, 30 mAmp, 35 mAmp, 40 mAmp, 45 mAmp, 50 mAmp, 60 mAmp, 70 mAmp, 80 mAmp, 90 mAmp, 100 mAmp, 125 mAmp, 150 mAmp, 175 mAmp, 200 mAmp, 225 mAmp, 250 mAmp, 275 mAmp, 300 mAmp, 325 mAmp, 350 mAmp, 375 mAmp, 400 mAmp, 425 mAmp, 450 mAmp, 475 mAmp, 500 mAmp, 525 mAmp, 550 mAmp, 575 mAmp, 600 mAmp, 625 mAmp, 650 mAmp, 675 mAmp, 700 mAmp, 725 mAmp, 750 mAmp, 775 mAmp, 800 mAmp, 825 mAmp, 850 mAmp, 875 mAmp, 900 mAmp, 925 mAmp, 950 mAmp, 975 mAmp, or 1000 mAmp. It will be appreciated that the control circuitry can be configured to direct the electric field generating circuit 2320 to deliver an electric field at a current falling within a range, wherein any of the forgoing currents can serve as the lower or upper bound of the range, provided that the lower bound of the range is a value less than the upper bound of the range.

In some embodiments, the control circuitry can be configured to direct the electric field generating circuit to deliver an electric field using voltages ranging from 1 $V_{rms}$ to 50 $V_{rms}$ to the site of a cancerous tumor. In some embodiments, the control circuitry can be configured to direct the electric field generating circuit to deliver an electric field using voltages ranging from 5 $V_{rms}$ to 30 $V_{rms}$ to the site of a cancerous tumor. In some embodiments, the control circuitry can be configured to direct the electric field generating circuit to deliver an electric field using voltages ranging from 10 $V_{rms}$ to 20 $V_{rms}$ to the site of a cancerous tumor.

In some embodiments, the control circuitry can be configured to direct the electric field generating circuit 320 to deliver an electric field using one or more voltages including 1 $V_{rms}$, 2 $V_{rms}$, 3 $V_{rms}$, 4 $V_{rms}$, 5 $V_{rms}$, 6 $V_{rms}$, 7 $V_{rms}$, 8 $V_{rms}$, 9 $V_{rms}$, 10 $V_{rms}$, 15 $V_{rms}$, 20 $V_{rms}$, 25 $V_{rms}$, 30 $V_{rms}$, 35 $V_{rms}$, 40 $V_{rms}$, 45 $V_{rms}$, or 50 $V_{rms}$. It will be appreciated that the control circuitry can be configured to direct the electric field generating circuit to deliver an electric field using a voltage falling within a range, wherein any of the forgoing voltages can serve as the lower or upper bound of the range, provided that the lower bound of the range is a value less than the upper bound of the range.

In some embodiments, the control circuitry can be configured to direct the electric field generating circuit to deliver and electric field using one or more frequencies including 10 kHz, 20 kHz, 30 kHz, 40 kHz, 50 kHz, 60 kHz, 70 kHz, 80 kHz, 90 kHz, 100 kHz, 125 kHz, 150 kHz, 175 kHz, 200 kHz, 225 kHz, 250 kHz, 275 kHz, 300 kHz, 325 kHz, 350 kHz, 375 kHz, 400 kHz, 425 kHz, 450 kHz, 475 kHz, 500 kHz, 525 kHz, 550 kHz, 575 kHz, 600 kHz, 625 kHz, 650 kHz, 675 kHz, 700 kHz, 725 kHz, 750 kHz, 775 kHz, 800 kHz, 825 kHz, 850 kHz, 875 kHz, 900 kHz, 925 kHz, 950 kHz, 975 kHz, 1 MHz. It will be appreciated that the electric field generating circuit can deliver an electric field using a frequency falling within a range, wherein any of the foregoing frequencies can serve as the upper or lower bound of the range, provided that the upper bound is greater than the lower bound.

In some embodiments, the control circuitry can be configured to direct the electric field generating circuit to generate one or more applied electric field strengths selected from a range of between 0.25 V/cm to 1000 V/cm. In some embodiments, the control circuitry can be configured to direct the electric field generating circuit to generate one or more applied electric field strengths of greater than 3 V/cm. In some embodiments, the control circuitry can be configured to direct the electric field generating circuit to generate one or more applied electric field strengths selected from a range of between 1 V/cm to 10 V/cm. In some embodiments, the control circuitry can be configured to direct the electric field generating circuit to generate one or more applied electric field strengths selected from a range of between 3 V/cm to 5 V/cm.

In other embodiments, the control circuitry can be configured to direct the electric field generating circuit to generate one or more applied electric field strengths including 0.25 V/cm, 0.5 V/cm, 0.75 V/cm, 1.0 V/cm, 2.0 V/cm, 3.0 V/cm, 5.0 V/cm, 6.0 V/cm, 7.0 V/cm, 8.0 V/cm, 9.0 V/cm, 10.0 V/cm, 20.0 V/cm, 30.0 V/cm, 40.0 V/cm, 50.0 V/cm, 60.0 V/cm, 70.0 V/cm, 80.0 V/cm, 90.0 V/cm, 100.0 V/cm, 125.0 V/cm, 150.0 V/cm, 175.0 V/cm, 200.0 V/cm, 225.0 V/cm, 250.0 V/cm, 275.0 V/cm, 300.0 V/cm, 325.0 V/cm, 350.0 V/cm, 375.0 V/cm, 400.0 V/cm, 425.0 V/cm, 450.0 V/cm, 475.0 V/cm, 500.0 V/cm, 600.0 V/cm, 700.0 V/cm, 800.0 V/cm, 900.0 V/cm, 1000.0 V/cm. It will be appreciated that the electric field generating circuit can generate an electric field having a field strength at a treatment site falling within a range, wherein any of the foregoing field strengths can serve as the upper or lower bound of the range, provided that the upper bound is greater than the lower bound.

It should be noted that, as used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

It should also be noted that, as used in this specification and the appended claims, the phrase "configured" describes a system, apparatus, or other structure that is constructed or configured to perform a particular task or adopt a particular configuration. The phrase "configured" can be used interchangeably with other similar phrases such as arranged and configured, constructed and arranged, constructed, manufactured and arranged, and the like.

All publications and patent applications in this specification are indicative of the level of ordinary skill in the art to which this invention pertains. All publications and patent applications are herein incorporated by reference to the same extent as if each individual publication or patent application was specifically and individually indicated by reference.

The embodiments described herein are not intended to be exhaustive or to limit the invention to the precise forms disclosed in the following detailed description. Rather, the embodiments are chosen and described so that others skilled in the art can appreciate and understand the principles and practices. As such, aspects have been described with reference to various specific and preferred embodiments and techniques. However, it should be understood that many variations and modifications may be made while remaining within the spirit and scope herein.

The invention claimed is:

1. A medical device system for treating a cancerous tissue, comprising:
   an implantable medical device comprising:
      an electric field generating circuit configured to generate one or more electric fields at or near a site of the cancerous tissue;
      control circuitry in communication with the electric field generating circuit, the control circuitry configured to control delivery of the one or more electric fields from the electric field generating circuit to the site of the cancerous tissue;
      wherein the control circuitry causes the electric field generating circuit to generate the one or more electric fields at frequencies selected from a range of between 10 kHz to 1 MHz using currents ranging from 1 mAmp to 1000 mAmp; and
   an implantable lead comprising:
      a lead body comprising a proximal end and a distal end, the lead body comprising a first electrical conductor disposed within the lead body; and
      a first electrode coupled to the lead body, the first electrode in electrical communication with the first electrical conductor, wherein the first electrical conductor forms part of an electrical circuit by which the electric fields from the electric field generating circuit are delivered to the site of the cancerous tissue; and
      a stent coupled to the lead body at a distal portion thereof;
      wherein the stent comprises a stent frame formed of a bioerodible material.

2. The medical device system of claim 1, wherein the stent frame serves as the first electrode.

3. The medical device system of claim 1, wherein the first electrode is disposed on an outside surface of the stent.

4. The medical device system of claim 1, wherein the stent comprises a stent frame formed of an electrically conductive material, wherein the stent frame is coated with a conductive fluid or gel.

5. The medical device system of claim 1, wherein the stent is a rigid stent that does not expand or contract.

6. The medical device system of claim 1, wherein the bioerodible material comprises a bioerodible metal.

7. A medical device system for treating a cancerous tissue, comprising:
   an implantable medical device comprising:
      an electric field generating circuit configured to generate one or more electric fields at or near a site of the cancerous tissue;
      control circuitry in communication with the electric field generating circuit, the control circuitry configured to control delivery of the one or more electric fields from the electric field generating circuit to the site of the cancerous tissue;
      wherein the control circuitry causes the electric field generating circuit to generate the one or more electric fields at frequencies selected from a range of between 10 kHz to 1 MHz using currents ranging from 1 mAmp to 1000 mAmp; and
   an implantable lead comprising:
      a lead body comprising a proximal end and a distal end, the lead body comprising a first electrical conductor disposed within the lead body; and
      a first electrode coupled to the lead body, the first electrode in electrical communication with the first electrical conductor, wherein the first electrical conductor forms part of an electrical circuit by which the electric fields from the electric field generating circuit are delivered to the site of the cancerous tissue; and
      a stent coupled to the lead body at a distal portion thereof;

wherein the stent comprises a stent frame formed of an electrically conductive bioerodible material;
wherein the stent frame is coated with a conductive gel.

8. The medical device system of claim 7, wherein the stent frame serves as the first electrode.

9. The medical device system of claim 7, wherein the first electrode is disposed on an outside surface of the stent.

10. The medical device system of claim 7, wherein the stent is a rigid stent that does not expand or contract.

11. The medical device system of claim 7, wherein the conductive gel comprises a chemotherapeutic agent.

12. The medical device system of claim 6, wherein the bioerodible metal is magnesium alloy.

* * * * *